US008039502B2

(12) United States Patent
Chen et al.

(10) Patent No.: US 8,039,502 B2
(45) Date of Patent: Oct. 18, 2011

(54) ANTI-INFECTIVE AGENTS AGAINST INTRACELLULAR PATHOGENS

(75) Inventors: Ching-Shih Chen, Upper Arlington, OH (US); Hao-Chieh Chiu, Columbus, OH (US); Dasheng Wang, Dublin, OH (US); John S. Gunn, Powell, OH (US); Larry S. Schlesinger, Powell, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 415 days.

(21) Appl. No.: 12/179,134

(22) Filed: Jul. 24, 2008

(65) Prior Publication Data

US 2009/0111799 A1    Apr. 30, 2009

Related U.S. Application Data

(60) Provisional application No. 60/951,672, filed on Jul. 24, 2007, provisional application No. 60/952,158, filed on Jul. 26, 2007.

(51) Int. Cl.
*C07D 231/12* (2006.01)
*A61K 31/415* (2006.01)

(52) U.S. Cl. .................. 514/406; 548/364.4; 548/364.1; 548/377.1

(58) Field of Classification Search ............... 548/364.4, 548/364.1, 377.1; 514/406
See application file for complete search history.

(56) References Cited

U.S. PATENT DOCUMENTS

| | | | |
|---|---|---|---|
| 5,091,387 | A | 2/1992 | Evans et al. |
| 5,134,142 | A | 7/1992 | Matsuo |
| 5,206,240 | A | 4/1993 | Baldwin et al. |
| 5,466,823 | A | 11/1995 | Talley |
| 5,521,207 | A | 5/1996 | Graneto |
| 5,550,147 | A | 8/1996 | Matsuo |
| 5,639,777 | A | 6/1997 | Lee |
| 5,670,509 | A | 9/1997 | Evans et al. |
| 5,760,068 | A | 6/1998 | Talley |
| 5,972,986 | A | 10/1999 | Seibert |
| 6,025,353 | A | 2/2000 | Masferrer |
| 7,026,346 | B2 | 4/2006 | Chen |
| 7,183,306 | B2 | 2/2007 | Shirai |
| 7,576,116 | B2 | 8/2009 | Chen |
| 2002/0032238 | A1 | 3/2002 | Priepke |
| 2003/0162824 | A1 | 8/2003 | Krul |
| 2003/0236294 | A1 | 12/2003 | Chen et al. |
| 2004/0116475 | A1 | 6/2004 | Shirai et al. |
| 2006/0079566 | A1 | 4/2006 | Chen |
| 2006/0142368 | A1 | 6/2006 | Chen et al. |
| 2008/0146815 | A1 | 6/2008 | Chen et al. |
| 2008/0269309 | A1 | 10/2008 | Chen |

FOREIGN PATENT DOCUMENTS

| | | |
|---|---|---|
| EP | 431943 | 6/1991 |
| EP | 444945 | 9/1991 |
| EP | 554829 | 8/1993 |
| EP | 418845 | 3/1997 |
| EP | 1512396 | 3/2005 |
| SG | 120841 | 7/2007 |
| WO | 95/15315 | 6/1995 |
| WO | 96/41626 | 12/1996 |
| WO | 03/086287 | 10/2003 |
| WO | 2005/044130 | 5/2005 |
| WO | 2008/130669 | 10/2008 |

OTHER PUBLICATIONS

Notice of Allowance from U.S. Appl. No. 10/409,502 dated Oct. 25, 2005.
Response from U.S. Appl. No. 10/409,502 dated Aug. 17, 2005.
Office action from U.S. Appl. No. 10/409,502 dated Feb. 17, 2005.
Response from U.S. Appl. No. 10/409,502 dated Dec. 16, 2004.
Office action from U.S. Appl. No. 10/409,502 dated Jul. 16, 2004.
Office action from U.S. Appl. No. 10/957,925 dated Mar. 30, 2007.
Response from U.S. Appl. No. 10/957,925 dated Jan. 4, 2007.
Office action from U.S. Appl. No. 10/957,925 dated Oct. 4, 2006.
Written Opinion from International Application No. PCT/US04/32723 dated Jul. 25, 2005.
International Search Report from International Application No. PCT/US04/32723 dated Jul. 25, 2005.
International Search Report from International Application No. PCT/US03/10738 dated Jan. 21, 2004.
Written Opinion from International Application No. PCT/US03/10738 dated Jun. 4, 2004.
Supplemental Search Report from European Application No. 03723936 dated Dec. 2, 2005.
Supplemental Search Report from European Application No. 04816902 dated Jul. 26, 2007.
Examination Report from European Application No. 03723936 dated Oct. 30, 2007.
Office action from Chinese Application No. 0661255 dated Dec. 7, 2007.
Birmingham et al., "Autophagy controls *Salmonella* infection in response to damage to the *Salmonella*-containing vacuole", J Biol Chem 281, pp. 11374-11383 (2006).
HCAPLUS 1994:8589, CAS Registry No. 151506-47-7, (1994).
Product catalog, Cayman Chemical Company, item 10008005 (OSU03012), May 2006, 3 pgs, (2006).
Gutierrez et al., "Autophagy is a defense mechanism inhibiting BCG and Mycobacterium tuberculosis survival in infected macrophages", Cell 119, pp. 753-766 (2004).
Buchdunger et al., "Inhibition of the Abl Protein-Tyrosine Kinase in Vitro and in Vivo by a 2-Phenylaminopyrimidine Derivative" Cancer Research 56, 100-104, (1996).
Devleeschauwer et al., "Remarkably Mild and Simple Preparations of Sulfinates, Sulfonyl Chlorides and Sulfonamides from Thioanisoles", Synlett, Thieme International, Stuttgart, DE, No. 4, 375-377 (Apr. 1997).
Groesch et al. (2001): STN International CAPLUS database, Columbus (Ohio), Accession No. 2001: 912333.
Johnson et al., "A novel celecoxib derivative, OSU03012, induces cytotoxicity in primary CLL cells and transformed B-cell lymphoma via a caspase and Bcl-2 independent mechanism", Blood First Edition Paper, prepublished online Sep. 28, 2004.
Nakagawa et al., "Autophagy defends cells against invading group A Streptococcus", Science 306, pp. 1037-1040 (2004).
Penning et al., "Synthesis and biological evaluation of the 1,5-diarylpyrazole class of cyclooxygenase-2 inhibitors: identification of 4-5[4-methylpheny1)-3-(trifluoromethyl)-1H-pyrazol-1-yl]benzenesulfonamide (SC-58635, celecoxib)," J Med Chem, 40: 1347-65 (1997).
Yacoub et al., "OSU-03012 Promoted Caspase-independent but PERK-, Cathepsin B-, BID-, and AIF-dependent killing of transformed cells", Molecular Pharmacology Fast Forward, first published on Apr. 18, 2006.
Yacoub et al., "OSU-03012 regulates cell growth in vitro of human glioma cells", Abstract from http://www.dominican.edu/query/ncur/display_ncur.php?id+2387, printed Jul. 24, 2007, 2 pgs.
Zhao et al., "The phospohonositide-dependent kinase-1 inhibitor, OSU-03012, prevents Y-box binding protein-1 (YB-1) from inducing epidermal growth factor receptor (EGFR)", Molecular Pharmacology Fast Forward, published on Jun. 26, 2007.
Response from U.S. Appl. No. 10/957,925 dated Aug. 18, 2006.
Office action from U.S. Appl. No. 10/957,925 dated Apr. 18, 2006.
Office action from U.S. Appl. No. 11/354,528 dated Jan. 31, 2008.
Response to Restriction from U.S. Appl. No. 11/864,612 dated Jan. 20, 2009.
Notice of Allowance from U.S. Appl. No. 11/864,612 dated Apr. 10, 2009.
Office action from U.S. Appl. No. 12/118,788 dated Jul. 26, 2010.
Amendment from U.S. Appl. No. 12/118,788 dated Oct. 21, 2010.
Notice of Allowance from U.S. Appl. No. 12/118,788 dated Dec. 1, 2010.
Office action from U.S. Appl. No. 12/476,772 dated Sep. 7, 2010.
Amendment from U.S. Appl. No. 12/476,772 dated Dec. 7, 2010.
Amendment from U.S. Appl. No. 12/476,772 dated Dec. 20, 2010.
Office action from Canadian Application No. 2,566,846 dated Dec. 2, 2010.
Office action from Chinese Application No. 200480036007.3 dated Dec. 7, 2007.
Amendment from Chinese Application No. 200480036007.3 dated May 30, 2008.
Office action from Chinese Application No. 200480036007.3 dated Jul. 18, 2008.
Amendment from Chinese Application No. 200480036007.3 dated Sep. 24, 2008.
Office action from Chinese Application No. 200480036007.3 dated Nov. 7, 2008.
Amendment from Chinese Application No. 200480036007.3 dated Mar. 20, 2009.
Communication from European Application No. 10005407.1 dated Aug. 18, 2010.
Office action from Indian Application No. 1131/CHENP/2006 dated Sep. 15, 2010.
Office action from Japanese Application No. 2006-534245 dated Jul. 28, 2010.
Response from Japanese Application No. 2006-534245 dated Oct. 27, 2010.
Office action from Japanese Application No. 2006-534245 dated Nov. 18, 2010.
Ahlstrom et al., "CYP2C9 structure-metabolism relationships: Optimizing the metabolic stability of COX-2 inhibitors", J of Medicinal Chemistry, vol. 50, No. 18, pp. 4444-4442, Sep. 6, 2007.
Fustero et al., "Improved regioselectivity in pyrazole formation through the use of fluorinated alcohols as solvents: Synthesis and biological activity of fluorinated tebufenpyrad analogs", J. of Organic Chemistry, vol. 73, No. 9, pp. 3523-3529, May 2, 2008.
Habeeb et al., "Design and Synthesis of Celecobix and Rofecobix analogues as selective cyclooxygenase-2 (COX-2) Inhibitors: Replacement of Sulfonamide and Methylsulfonyl pharmacophores by an Azido Bioisostere", J. of Medicinal Chemistry, American Chemical Society, Washington, US, vol. 44, No. 1, pp. 3039-3042, Jan. 1, 2001.
Singh et al., "Methanesulfonamide group at position-4 of the C-5-phenyl ring of 1,5-diarylpyrazole affords a potent class of cyclooxygenase-2 (COX-2) inhibitors", Bioorganic and Medicinal Chemistry Letters, vol. 14, No. 7, pp. 1683-1688, Apr. 2004.
Sloop et al., "Synthesis of fluorinated heterocycles", J. of Fluorine Chemistry, Elsevier, vol. 118, No. 1-2, pp. 135-147, Dec. 1, 2002.
Sosnovikikh et al., "2-Polyfluoroalkylchromones", Russian Chemical Bulletin, International Edition, vol. 51, No. 7, pp. 1280-1291, 2002.
Uddin et al., "Design and synthesis of novel celecoxib analogues as selective cyclooxygenase-2 (COX-2) inhibitors: Replacement of the sulfonamide pharmacophore by a sulfonylazide bioisostere", Bioorganic and Medicinal Chemistry, vol. 11, No. 23, pp. 5273-5280, Nov. 17, 2003.
Database CA, Chemical Abstracts Service, Columbus, Ohio XP002595201 retrieved from STN Database accession No. 2004:944309; & CN 1468854, Jan. 21, 2004.
Notice of Allowance from U.S. Appl. No. 12/476,772 dated Jan. 26, 2011.
Jenkins et al., "Drug Eluting Coronary Stents", BMJ, vol. 235, Dec. 7, 2002, pp. 1315-1316.
Farb et al., "Oral Everolimus Inhibits iln-Stent Neointimal Growth", Circulation, 2002, vol. 106, pp. 2379-2384.

Schonthal, Ah., "Direct non-cyclooxygenase-2 targets of celeoxib and their potential relevance for cancer therapy," British Journal of Cancer (2007) 97, pp. 1465-1468.

*Primary Examiner* — Kahsay T Habte
(74) *Attorney, Agent, or Firm* — Calfee, Halter & Griswold LLP

(57) ABSTRACT

A new class of phosphoinositide-dependent kinase-1 (PDK-1) inhibitors of Formula I:

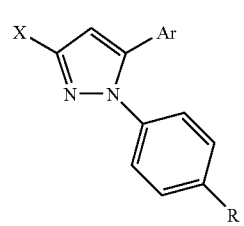

wherein X wherein X is —$CF_3$, Ar is selected from

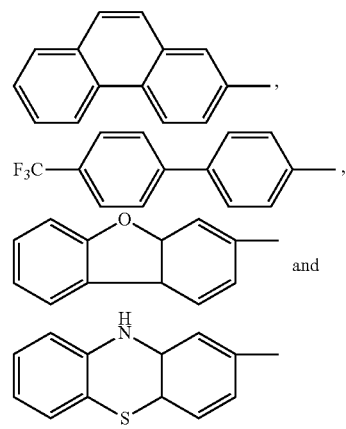

and R is selected from

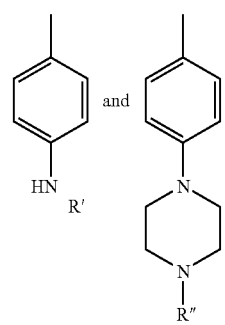

where
R' is L-Lys, D-Lys, β-Ala, L-Lue, L-Ile, Phe, $SO_2CH_2CH_2NH_2$, $SO_2NH_2$, Asn, Glu or Gyl, and
R" is methyl, ethyl, allyl, $CH_2CH_2OH$, $CH_2CN$, $CH_2CH_2CN$, $CH_2CONH_2$,

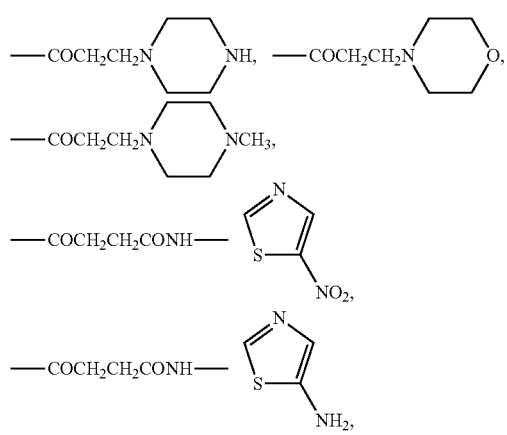
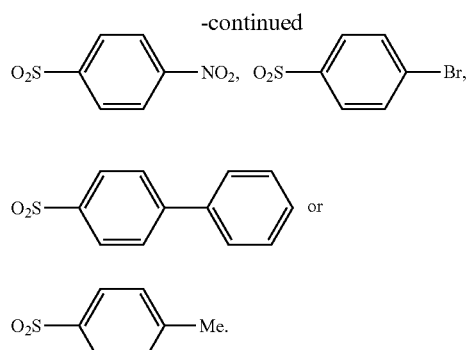
15 Claims, 6 Drawing Sheets

ANTI-INFECTIVE AGENTS AGAINST INTRACELLULAR PATHOGENS

CROSS-REFERENCE TO RELATED APPLICATIONS

This application is based on U.S. Provisional application Ser. No. 60/951,672, filed Jul. 24, 2007, as well as U.S. Provisional application Ser. No. 60/952,158, filed Jul. 26, 2007, the priorities for which are hereby claimed and the disclosures of which are hereby incorporated herein by reference in their entirety.

STATEMENT REGARDING FEDERALLY FUNDED RESEARCH

This invention was made, at least in part, with government support under National Institutes of Health Grant CA94829 and Army Grant DAMD 17-02-1-0117. The government may have certain rights in this invention.

BACKGROUND

Figure 4:
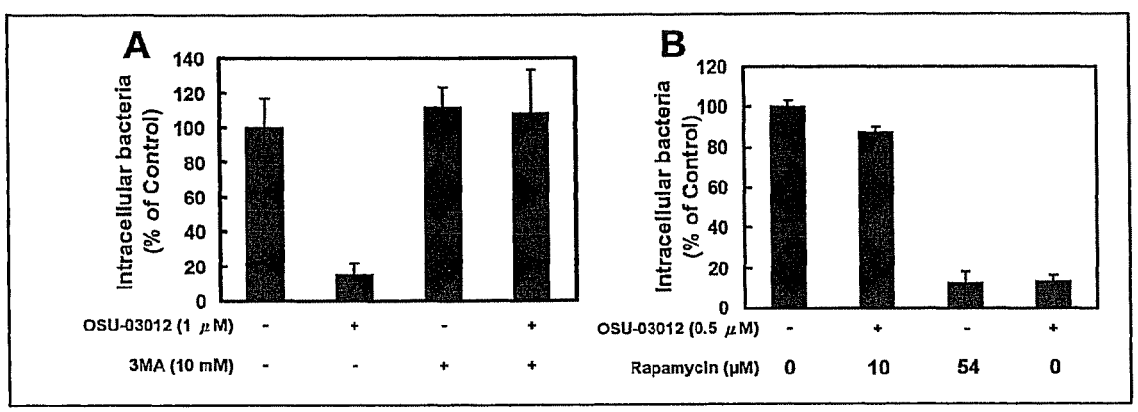

*Francisella tularensis* is a facultative, intracellular, Gram-negative bacterium that is the causative agent of tularemia, a severe and potentially lethal zoonotic disease. This NIAID Category A pathogen has been recognized for several decades as a potential threat to public health as a bioweapon for a number of reasons. These include its ability to infect via multiple routes, the very low infectious dose required to cause serious disease, the acquisition by aerosol exposure of respiratory tularemia, the most debilitating and lethal form of the disease, and the ease with which aerosolized organisms could be widely disseminated. In light of recent concerns about bioterrorism, the development of new therapies to defend against the use of *F. tularensis* as a biological weapon is a priority.

Autophagy is a mechanism of cellular homeostasis in which cytoplasmic material is sequestered in characteristic vacuoles called autophagosomes and then delivered to lysosomes for degradation. This evolutionarily conserved process provides for the recycling of long-lived cytosolic proteins to fulfill cellular needs for energy and survival in response to environmental stress or nutrient deprivation, and for the removal of excess or damaged organelles which may serve to protect cells from apoptosis. Recent studies have established a role for autophagy in cellular defense against intracellular pathogens including bacteria, such as *Mycobacterium tuberculosis, Streptococcus pyogenes, Shigella* spp. and *Salmonella typhimurium*, as well as viruses and protozoa. The execution of autophagy is regulated by upstream signal transduction systems that are influenced by largely physiological factors such as nutrient status, growth factors/cytokines, and hypoxia. The pharmacological induction of autophagy represents an intriguing and unexploited therapeutic strategy in which this effector of innate immunity would be triggered or amplified to defend against intracellular pathogens.

OSU-03012 (formula XV), a PDK-1/Akt signaling inhibitor, is one of many distinct classes of molecularly targeted agents developed by the inventors. OSU-03012 was derived through structure-based optimization of the COX-2 inhibitor, celecoxib, with regard to PDK-1 activity. Based in part on the novelty of its molecular target and its importance in cancer cell survival, the compound entered into preclinical evaluation through the NCI RAID program. Investigation of OSU-03012 revealed that it induces autophagy with a sub-/μM IC50. This point is noteworthy for two reasons. First, concentrations in this range are clearly attainable in the in vivo preclinical and clinical settings. Second, this $IC_{50}$ for autophagy induction is quite a bit lower than that for inhibition of PDK-1 activity (~5 μM), which suggests a mechanism distinct from inhibition of PDK-1/Akt signaling.

SUMMARY OF THE INVENTION

Provided are compounds of Formula I that induce autophagy and/or defend a host against intracellular pathogens:

I 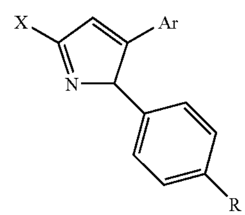 wherein X is selected from alkyl and haloalkyl; Ar is selected from the group consisting of phenyl, biphenyl, naphthyl, anthryl, phenanthryl, and fluorenyl; R is selected from the group consisting of $-CN$, $-CH_2CN$, $-CH_2CH_2CN$, $-CH_2CH_2CH_2CN-CONH_2$ ,
,
,
,
,
,
,
, and
.

Formula I also includes pharmaceutically acceptable salts thereof, metabolism products, and prodrugs thereof. Also, provided are compounds of formulae II-XIV that induce autophagy and/or defend a host against intracellular pathogens. Formula II-XIV also includes pharmaceutically acceptable salts thereof, metabolism products, and prodrugs thereof.

BRIEF DESCRIPTION OF THE FIGURES

FIG. 1 shows dose-dependent effects of compound 34/70 (left panels) and compound 35/71 (right panels) on cell viability of PC-3 cells and on the cell growth in nine representative human tumor cell lines.

FIG. 2 shows the synthesis of compounds 25-36 (61-72) using the 1,1,1-trifluoro-4-hydroxy-4-phenanthren-2-yl-but-3-en-2-one as a common precursor.

FIG. 3 shows in panel A time-dependent and in panel B dose-dependent effects of OSU-03012 as assessed in intracellular survival (i.e. gentamicin protection) assays; and panel C shows the effect of OSU-03012 on extracellular bacterial growth in liquid medium.

FIG. 4 shows in panel A that 3-methyladenine (3MA) completely blocked the ability of OSU-03012 to reduce intracellular bacterial survival; and panel B shows that rapamycin, an established inducer of autophagy, is also capable of suppressing survival of *S. typhimurium* in murine macrophages.

Figure 5:
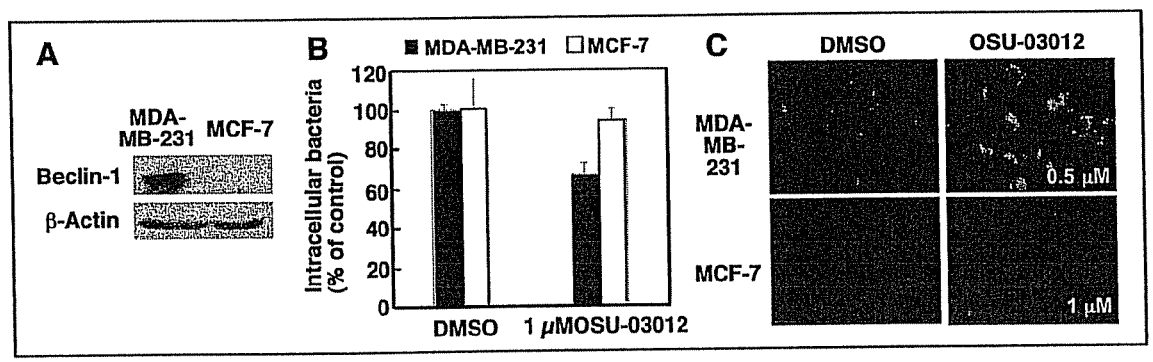

FIG. 5 shows in panel A that the human breast cancer cell lines, MCF-7 and MDA-MB-231, differ in their expression levels of beclin-1, a tumor suppressor that is critical for the execution of autophagy; panel B shows that intracellular bacterial survival in OSU-03012-treated *S. typhimurium*-infected breast cancer cells also reflects their respective beclin-1 status; and panel C shows that the ability of OSU-03012 to induce autophagy in these cell lines, as determined by the intensity of immunostaining for endogenous LC3, a marker of mammalian autophagosomes, correlates with their respective beclin-1 expression levels.

Figure 6:
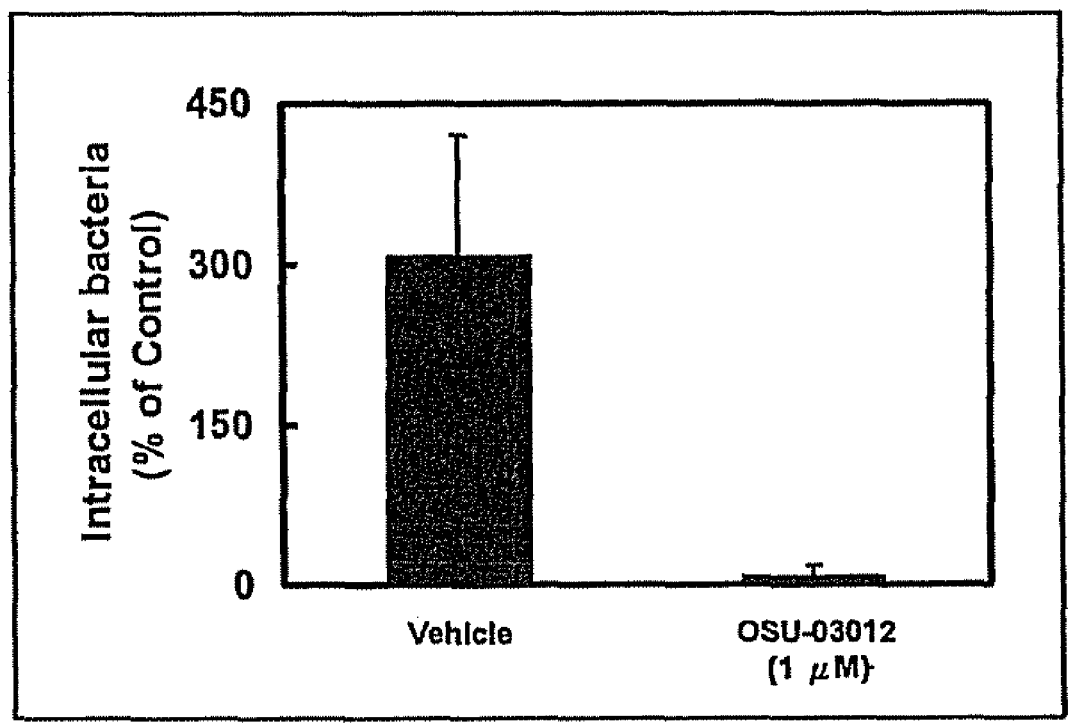

FIG. 6 shows that OSU-03012 reduced intracellular survival of *F. novicida*.

DETAILED DESCRIPTION

Due to cell membrane barriers, antibiotic treatment is ineffective against intracellular bacteria as most antibiotics are unable to penetrate the cell membrane or will be excluded by host cells. Even if an antibiotic can enter cells, intracellular bacterial growth might cause a transient antibiotic-resistance, causing a need of higher doses of antibiotics kill the intracellular bacteria. On the other hand, host cells developed innate immunity that employs different strategies to defend against intracellular pathogens. Given the importance of autophagy as an immune defense mechanism against intracellular pathogens, the ability of OSU-03012 and derivatives to eliminate intracellular bacteria in macrophages was tested. OSU-03012 and derivatives (Formulae I-XV) promote intracellular bacterial clearance by inducing autophagy in the host macrophage at physiologically attainable concentrations. Thus, OSU-03012 and derivatives are anti-infective agents for the treatment of diseases caused by intracellular pathogens, including, but not limited to, *Mycobacterium tuberculosis* (tuberculosis), *Francisella tularensis* (pulmonary tularemia), Group A *Streptococcus pyogenes*, *Rickettsiae* spp., and *Salmonella typhimurium*. OSU-03012 and derivatives can also be used as autophagy-inducing agents to treat viral infections and neurodegenerative diseases.

These small-molecule autophagy-inducing agents (Formulae I-XV) activate an innate defense mechanism in macrophage to eradicate bacterial hiding inside host cells. In addition, these agents can be used in the prevention of septic shock, which occurs when high doses of antibiotics are used, by reducing the release of bacterial endotoxins.

The compounds described herein can be shown in the general Formula I:

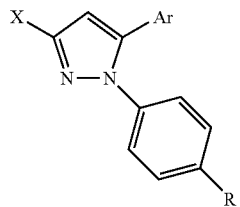

I wherein X is selected from alkyl and haloalkyl; Ar is selected from the group consisting of phenyl, biphenyl, naphthyl, anthryl, phenanthryl, and fluorenyl; R is selected from the group consisting of —CN, —CH$_2$CN, —CH$_2$CH$_2$CN, —CH$_2$CH$_2$CH$_2$CN, —CONH$_2$,

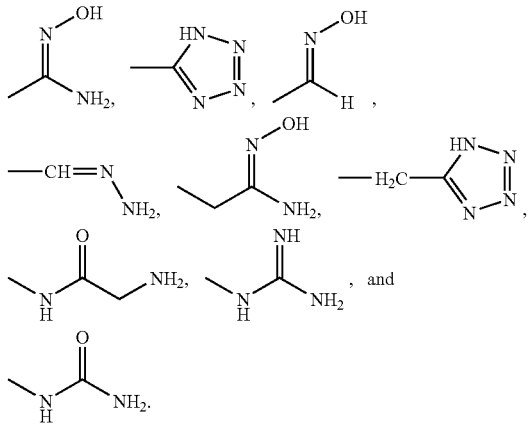

Stated otherwise, R is selected from nitrile, acetonitrile, ethylnitrile, propylnitrile, carboxyamide, amidine, pyrazole, oxime, hydrazone, acetamidine, acetamide, guanidine, and urea. Formula I also includes pharmaceutically acceptable salts thereof, metabolism products, and prodrugs thereof.

In some embodiments, X is C$_1$ to C$_4$ haloalkyl. In some embodiments, X is CF$_3$. In some embodiments, Ar may be substituted at any substitutable position with one or more radicals, such as, but not limited to halo, C$_1$-C$_4$ alkyl, C$_1$-C$_4$ haloalkyl, azido, C$_1$-C$_4$ azidoalkyl, aryl, alkylaryl, haloaryl, haloalkylaryl, and combinations thereof. In some embodiments, Ar is selected from 2-naphthyl, 4-biphenyl, 9-anthryl, 2-fluorenyl, 4-azidophenyl, 4-azidomethylphenyl, 4-(2-azidoethyl)phenyl, 4-(3-azidopropyl)phenyl, 4-(4-azidobutyl) phenyl, 4-(4-azidophenyl)phenyl, 4-(4-azidomethylphenyl) phenyl, 4-methylphenyl, 4-ethylphenyl, 4-propylphenyl, 4-butylphenyl, 4-(2-bromoethyl)phenyl, 4-(3-bromopropyl) phenyl, 4-(4-bromobutyl)phenyl, 4-(trifluoromethyl)phenyl, 4-(4-methylphenyl)phenyl, 4-(4-bromomethylphenyl)phenyl, 4-(4-butylphenyl)phenyl, 4-(4-tert-butylphenyl)phenyl, 2-chlorophenyl, 4-chlorophenyl, 2,4-dichlorophenyl, 3,4-dichlorophenyl, 2,5-dichlorophenyl, 2,4-dimethylphenyl, 2,5-dimethylphenyl, 3,4-dimethylphenyl, 3,5-dimethylphenyl, 4-(4-chlorophenyl)phenyl, 4-(3,5-dichlorophenyl)phenyl, 4-(2,3-dichlorophenyl)phenyl, 4-(3,5-dimethylphenyl) phenyl, 4-(2,4,5-trichlorophenyl)phenyl, 4-(4-trifluoromethylphenyl)phenyl, 2-phenanthrenyl, 3-indolyl, 2-pyrrolyl, and 4-(benzyl)phenyl. In some embodiments, Ar is selected from 4-(2-bromoethyl)phenyl, 4-(3-bromopropyl) phenyl, 4-(2-azidoethyl)phenyl; 4-(3-azidopropyl)phenyl, 4-butylphenyl, 4-t-butylphenyl, 2-naphthalenyl, 3-indolyl, 4-biphenylyl, 4'-chloro[1,1'-biphenyl]-4-yl, 3',5'-dichloro[1, 1'-biphenyl]-4-yl, 2',3'-dichloro[1,1'-biphenyl]-4-yl, 4'-methyl[1,1'-biphenyl]-4-yl, 4'-trifluoromethyl[1,1'-biphenyl]-4-yl, 4'-bromomethyl[1,1'-biphenyl]-4-yl, 3',5'-dimethyl[1, 1'-biphenyl]-4-yl, 4'-butyl[1,1'-biphenyl]-4-yl, 4'-tert-butyl [1,1'-biphenyl]-4-yl, 4-(phenylmethyl)phenyl, 9H-fluoren-2-yl, 9-anthracenyl, 2-phenanthrenyl, 9-phenanthrenyl. In some embodiments, Ar is 2-phenanthrenyl. In some embodiments, R is selected from aminoacetamide and guanidine.

Another embodiment described herein is that of Formula II:

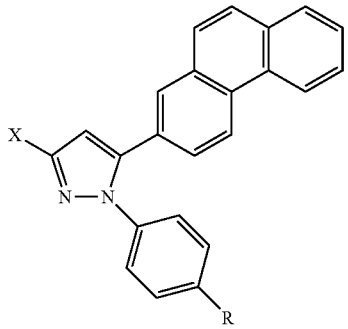

wherein X is selected from alkyl and haloalkyl; R is selected —CN, —CH₂CN, —CH₂CH₂CN, —CH₂CH₂CH₂CN —CONH₂

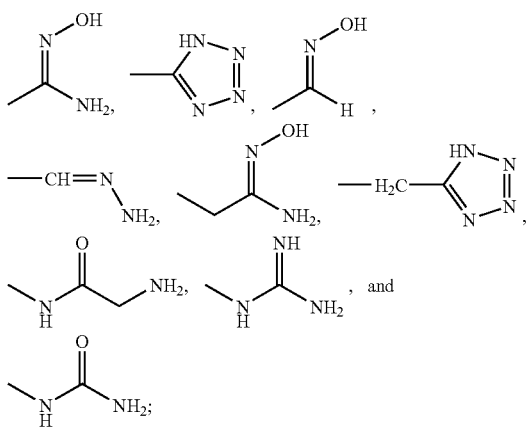

or stated otherwise, R is selected from nitrile, acetonitrile, ethylnitrile, propylnitrile, carboxyamide, amidine, pyrazole, oxime, hydrazone, acetamidine, acetamide, guanidine, and urea. In some embodiments, X is C₁ to C₄ haloalkyl, and in some embodiments, X is CF₃. In some embodiments, R is aminoacetamide or guanidine. Formula III also includes pharmaceutically acceptable salts thereof, metabolism products, and prodrugs thereof.

Another embodiment described herein is that of Formula III:

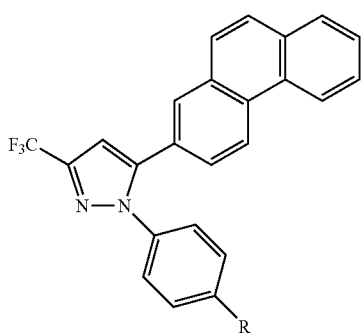

wherein R is selected from the group consisting of —CN, —CH₂CN, —CH₂CH₂CN, —CH₂CH₂CH₂CN —CONH₂

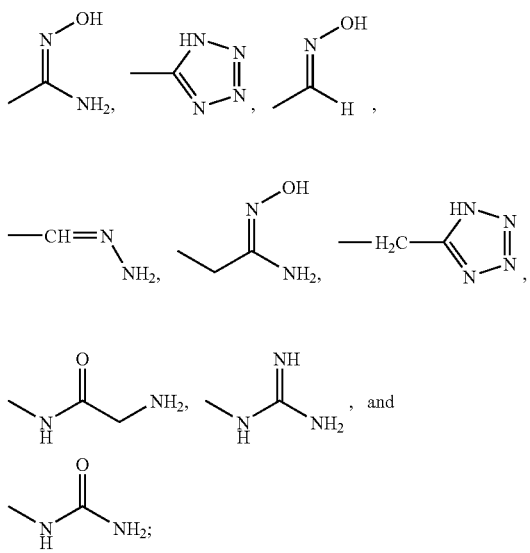

or stated otherwise, R is selected from nitrile, acetonitrile, ethylnitrile, propylnitrile, carboxyamide, amidine, pyrazole, oxime, hydrazone, acetamidine, acetamide, guanidine, and urea. In some embodiments, R is aminoacetamide or guanidine. Formula II also includes pharmaceutically acceptable salts thereof, metabolism products, and prodrugs thereof.

Some additional compounds of Formula III include the following groups for R:

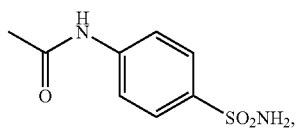

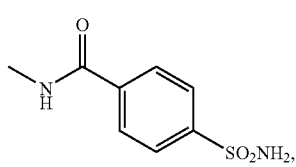

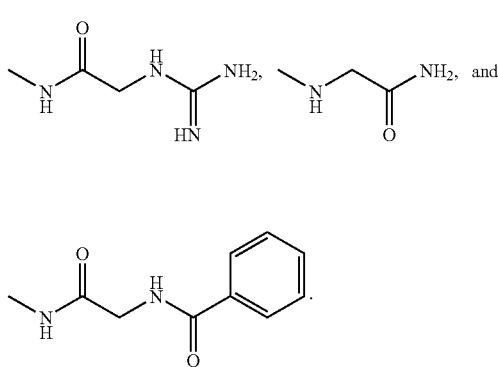

In another embodiment, the compounds are that of Formula IV or V:
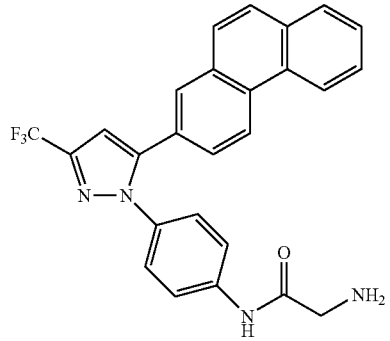
IV
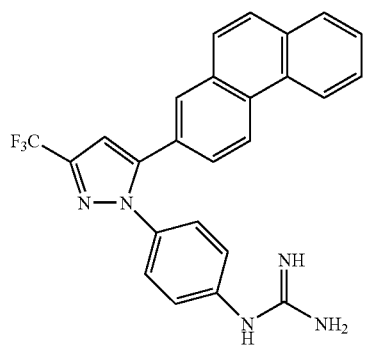
V
In other embodiments, the compounds are that of following Formulas VI-XIV:
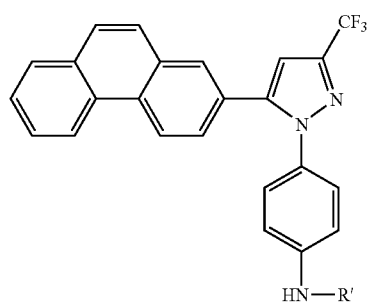
VI
R' = L-Lys, MW: 531.57
D-Lys, MW: 531.57
β-Ala, MW: 474.48
L-Lue
L-Ile
Phe
SO2CH2CH2NH2, MW: 510.53
SO2NH2, MW: 482.48
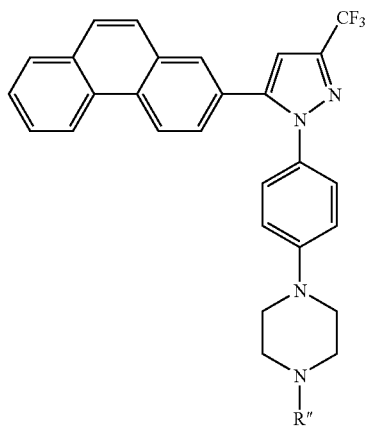
VII
R″ = H, MW: 472.50
Gly, MW: 529.56
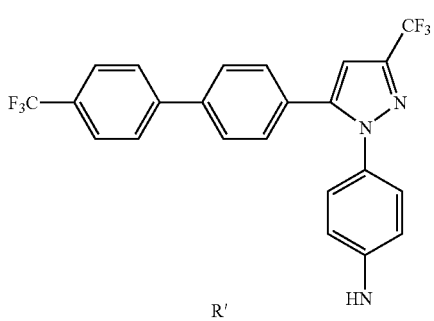
VIII
R' = Gly, MW: 504.43
β-Ala, MW: 518.45
L-Lys, MW: 575.55
D-Lys, MW: 575.55
L-Lue,
L-Ile,
Phe
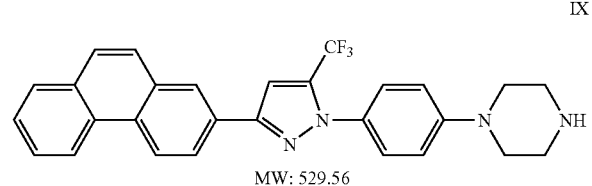
IX
MW: 529.56
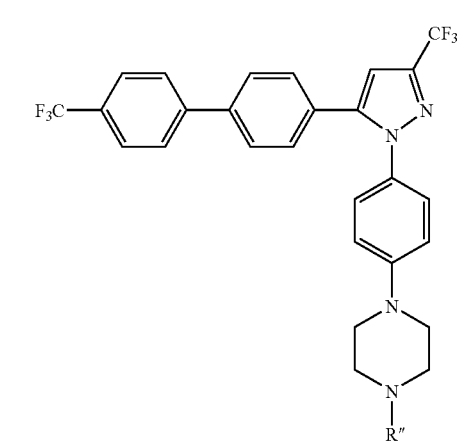
X
R″ = H,
Me,
2-Hydroxyethyl,
Allyl,

XI

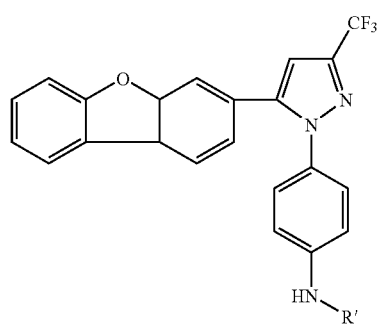

R' = Gly, MW: 452.43
b-Ala, MW: 466.46
L-Lys, MW: 523.55
D-Lys, MW: 523.55
Asn, MW: 524.49
Glu, MW: 538.52

XII

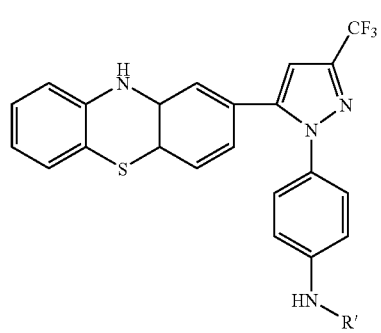

R' = Gly, MW: 483.51
β-Ala, MW: 497.54
L-Lys, MW: 554.63
D-Lys, MW: 554.63

In still another embodiment, the compounds are that of following Formula XIII:

XIII

[Structure of Formula XIII: 4'-(trifluoromethyl)biphenyl connected to pyrazole with CF3, N-phenyl-piperazine-R'']

| | | |
|---|---|---|
| F4ME | R'' = Me | MW 530.51 |
| F4E | R'' = Et | MW 544.54 |
| F4HE | R'' = CH2CH2OH | MW 560.53 |

XIII

[Structure of Formula XIII: 4'-(trifluoromethyl)biphenyl connected to pyrazole with CF3, N-phenyl-piperazine-R'']

| | | |
|---|---|---|
| F4ETFM | R'' = CH2CH2CF3 | MW 612.53 |
| F4ACN | R'' = CH2CN | MW 555.52 |
| F4PCN | R'' = CH2CH2CN | MW 569.54 |
| F4AP | R'' = —COCH2CH2-(piperazine-NH) | MW 573.53 |
| F4AMO | R'' = —COCH2CH2-(morpholine) | MW 574.52 |
| F4AMP | R'' = —COCH2CH2-(N-methylpiperazine) | MW 587.56 |
| F4AANT | R'' = —CH2CH2CONH—(5-nitrothiazol-2-yl) | MW 632.54 |
| F4AAT | R'' = —CH2CH2CONH—(5-aminothiazol-2-yl) | MW 602.55 |
| F4AA | R'' = CH2CONH2 | |
| F4PA | R'' = CH2CH2CONH2 | |

In a still another embodiment, the compound has the following Formula XIV:

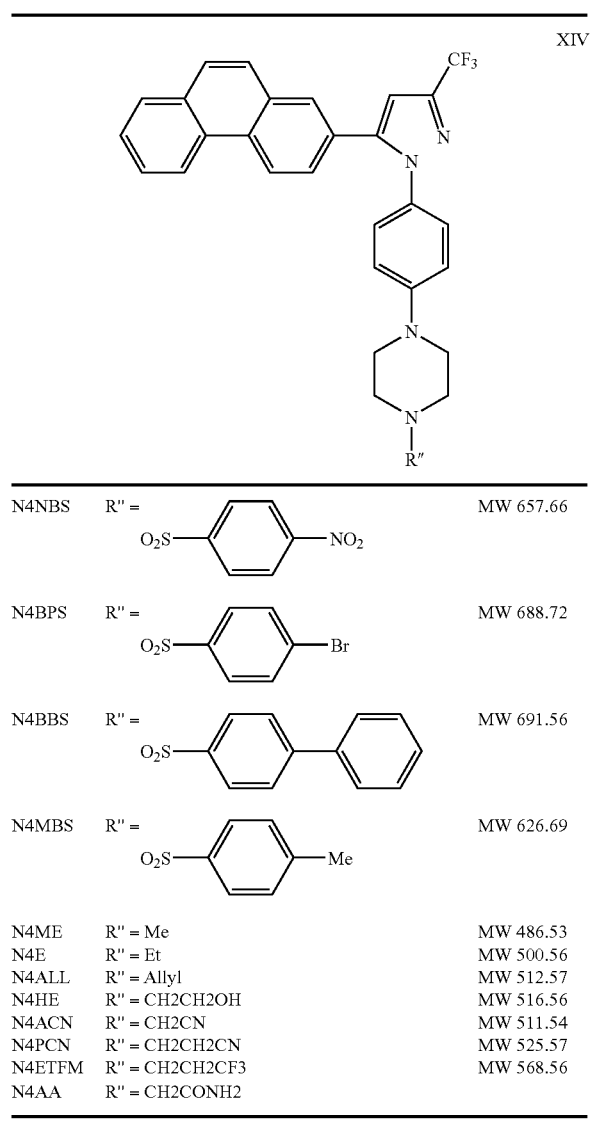

| | | |
|---|---|---|
| N4NBS | R″ = –O₂S–C₆H₄–NO₂ | MW 657.66 |
| N4BPS | R″ = –O₂S–C₆H₄–Br | MW 688.72 |
| N4BBS | R″ = –O₂S–C₆H₄–C₆H₅ | MW 691.56 |
| N4MBS | R″ = –O₂S–C₆H₄–Me | MW 626.69 |
| N4ME | R″ = Me | MW 486.53 |
| N4E | R″ = Et | MW 500.56 |
| N4ALL | R″ = Allyl | MW 512.57 |
| N4HE | R″ = CH2CH2OH | MW 516.56 |
| N4ACN | R″ = CH2CN | MW 511.54 |
| N4PCN | R″ = CH2CH2CN | MW 525.57 |
| N4ETFM | R″ = CH2CH2CF3 | MW 568.56 |
| N4AA | R″ = CH2CONH2 | |

In a still another embodiment, the compound has the following Formula XV:

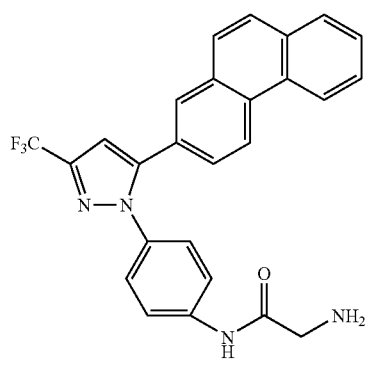

Generally, compounds of Formulas VI-XV (except for those formula IX) can be regarded as corresponding to formula I

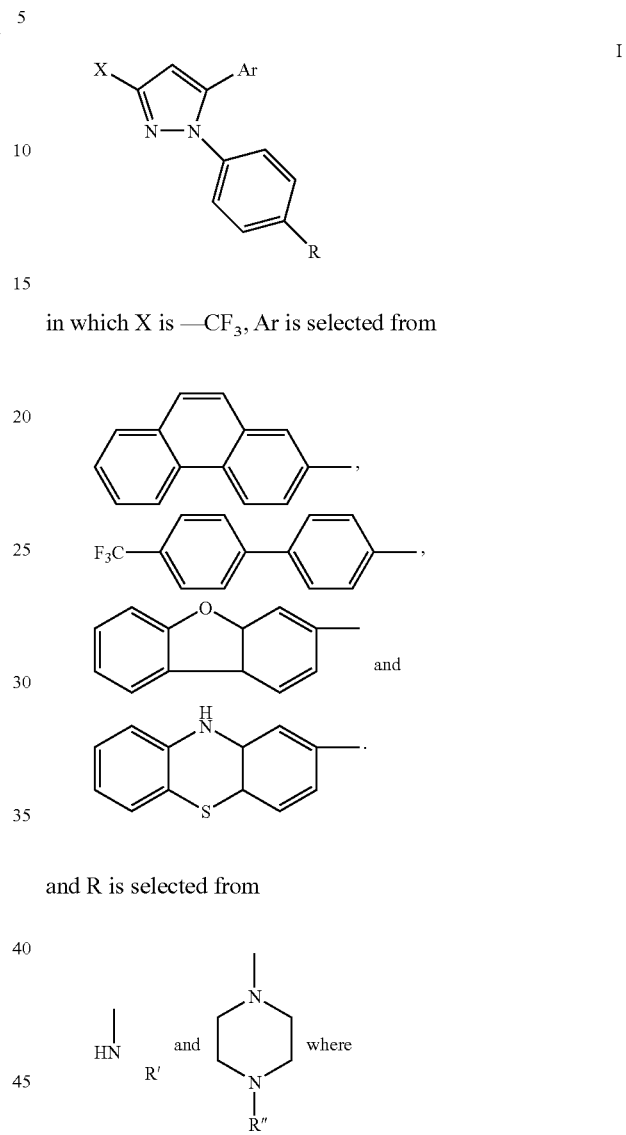

in which X is —CF₃, Ar is selected from

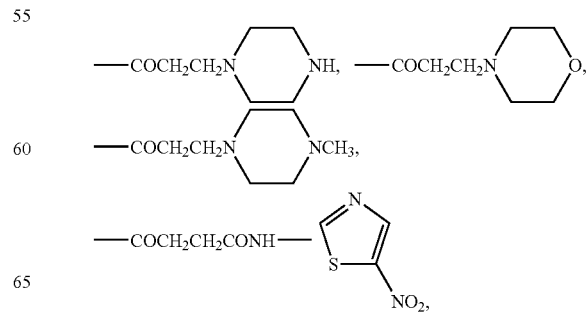

and R is selected from

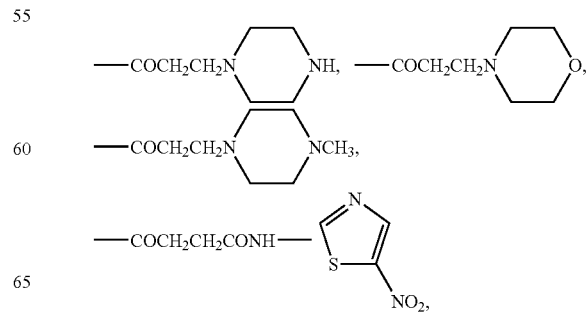

R′ is L-Lys, D-Lys, β-Ala, L-Lue, L-Ile, Phe, SO₂CH₂CH₂NH₂, SO₂NH₂, Asn, Glu or Gyl, and R″ is methyl, ethyl, allyl, CH₂CH₂OH, CH₂CN, CH₂CH₂CN, CH₂CONH₂,

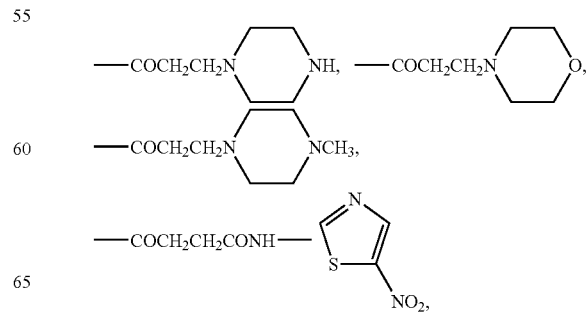

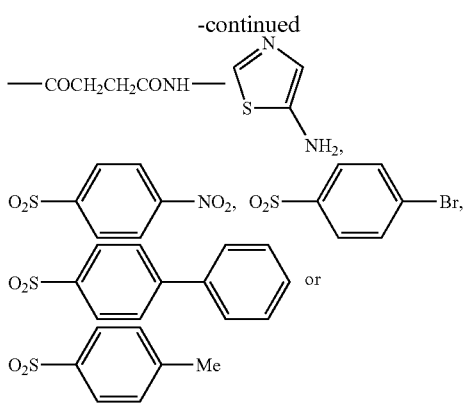

Provided also are methods of using the compounds of formulae I-XV to induce apoptosis in undesirable proliferating cells in subjects in need of such treatment. Also provided are methods of using compounds of formulae I-XV to induce autophagy in cells infected with intracellular pathogens in subjects in need of such treatment. The methods involve treating the subject in need of such treatment with a therapeutically effective amount of a compound of formulae I-XV or derivative, metabolites, or pharmaceutically acceptable salts thereof.

The compounds and methods described herein are useful for, but not limited to treating, inhibiting, or delaying the onset of cancers. The compounds and methods are also useful in the treatment of intracellular infections. The compounds and methods are also useful in the treatment of precancers and other incidents of undesirable cell proliferation. The compounds of formula I, II, III, IV, V, VI, VII, VIII, IX, X, XI, XII, XIII, XIV, or XV, or combinations thereof, are administered to a subject that has been diagnosed with or is at risk of developing a disorder characterized by undesirable cell proliferation. The compounds and methods are useful for treating cancers including, but not limited to, leukemia, melanoma, non-small cell lung cancer, colon cancer, cancers of the central nervous system, ovarian cancer, breast cancer, kidney cancer, and prostate cancer. Furthermore, they are useful in the slowing the growth of these cancers in individuals with precancers, as well as individuals prone to or having a genetic predisposition to these disorders.

The compounds are useful in methods of inducing apoptosis in unwanted rapidly proliferating cells, the method comprising introducing a therapeutically effective amount of a compound of formula I, II, III, IV, V, VI, VII, VIII, IX, X, XI, XII, XIII, XIV, or XV, or combinations thereof, to the unwanted rapidly proliferating cells. In accordance with this method, the unwanted rapidly proliferating cells may be cancer cells. The cancer cells may be selected from the group consisting of leukemia, melanoma, non-small cell lung cancer, colon cancer, cancers of the central nervous system, ovarian cancer, breast cancer, kidney cancer, and prostate cancer.

The compounds are further useful for preventing restenosis in a subject who has undergone an angioplasty or stent procedure comprising administering a therapeutically effective amount of a compound of formula I, II, III, IV, V, VI, VII, VIII, IX, X, XI, XII, XIII, XIV, or XV, or combinations thereof, or pharmaceutically acceptable salts and/or metabolites thereof to the subject who has undergone an angioplasty or stent procedure. XV, or combinations thereof, or pharmaceutically acceptable salts and/or metabolites thereof to the subject who has undergone an angioplasty or stent procedure.

The following terms used herein include, but are not limited to the following definitions:

The term "PDK-1/Akt signaling inhibitor" signifies that a specific compound or combination of compounds is capable of disrupting the PDK-1/Akt signaling pathway, as measured versus a blank, regardless of whether in vivo or in vitro. One method is set forth in the examples below, though other methods now known or later developed may also be used.

The term "treatment" as used herein, encompasses the administration and/or application of one or more compounds described herein, to a subject, for the purpose of providing prevention of or management of, and/or remedy for a condition. "Treatment" for the purposes of this disclosure, may, but does not have to, provide a cure; rather, "treatment" may be in the form of management of the condition. When the compounds described herein are used to treat unwanted proliferating cells, including cancers, "treatment" includes partial or total destruction of the undesirable proliferating cells with minimal destructive effects on normal cells. A desired mechanism of treatment of unwanted rapidly proliferating cells, including cancer cells, at the cellular level is apoptosis.

The term "prevention" as used herein includes either preventing or slowing the onset of a clinically evident unwanted cell proliferation altogether or preventing or slowing the onset of a preclinically evident stage of unwanted rapid cell proliferation in individuals at risk. Also intended to be encompassed by this definition is the prevention or slowing of metastasis of malignant cells or to arrest or reverse the progression of malignant cells. This includes prophylactic treatment of those at risk of developing precancers and cancers. Also encompassed by this definition is the prevention or slowing of restenosis in subjects that have undergone angioplasty or a stent procedure.

The terms "therapeutically effective" and "pharmacologically effective" are intended to qualify the amount of each agent which will achieve the goal of improvement in disease severity and the frequency of incidence over treatment with the compounds described herein. Therapeutically effective or pharmacologically effective amounts may readily be determined by those skilled in the art.

The term "subject" for purposes of treatment includes any human or animal subject who has been diagnosed with, has symptoms of, or is at risk of developing a disorder characterized by unwanted, rapid cell proliferation. Such disorders include, but are not limited to cancers and precancers. For methods of prevention the subject is any human or animal subject. To illustrate, for purposes of prevention, a subject may be a human subject who is at risk of or is genetically predisposed to obtaining a disorder characterized by unwanted, rapid cell proliferation, such as cancer. The subject may be at risk due to exposure to carcinogenic agents, being genetically predisposed to disorders characterized by unwanted, rapid cell proliferation, and so on. Besides being useful for human treatment, the compounds described herein are also useful for veterinary treatment of mammals, including companion animals and farm animals, such as, but not limited to dogs, cats, horses, cows, sheep, and pigs.

Dosage and Administration

Preliminary animal studies have shown that these compounds can be orally absorbed, can generate average serum concentrations several-fold higher than total growth inhibition (TGI), and more importantly, incur little toxicity to the animals after daily oral administration for one month (data not shown)

The compounds of the present invention can be formulated into suitable pharmaceutical preparations such as tablets, capsules, or elixirs for oral administration or in sterile solutions or suspensions for parenteral administration. The therapeutic agents described herein can be formulated into pharmaceutical compositions using techniques and procedures well known in the art.

The PDK-1/Akt signaling inhibitor described herein is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. In some embodiments, the dosage may be between 0.1 to 1000 mg of the PDK-1/Aft signaling inhibitor. In some embodiments, the compositions can be formulated in a unit dosage form, each dosage containing from 1 to 500 mg. In other embodiments, the dosage may be from 10 to 100 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient. The dosage may depend on many factors, such as the age and size of the subject, the condition being treated, the severity of the condition, and other factors known to those skilled in the art. Taking those factors into account, dosages can be determined by those skilled in the art.

To prepare compositions, one or more of the therapeutic agents employed in the methods of the invention are mixed with a suitable pharmaceutically acceptable carrier. Upon mixing or addition of the therapeutic agent(s), the resulting mixture may be a solution, suspension, emulsion, or the like. These may be prepared according to methods known to those skilled in the art. The form of the resulting mixture depends upon a number of factors, including the intended mode of administration and the solubility of the compound in the selected carrier or vehicle. The effective concentration is sufficient for inducing apoptosis in undesired cells, such as cancer cells, and may be empirically determined.

Pharmaceutical carriers or vehicles suitable for administration of the present therapeutic agents include any such carriers suitable for the particular mode of administration. In addition, the active materials can also be mixed with other active materials that do not impair the desired action, or with materials that supplement the desired action, or have another action. The present therapeutic agents may be formulated as the sole pharmaceutically active ingredient in the composition or may be combined with other active ingredients. Derivatives of the present therapeutic agents, such as salts or prodrugs, may also be used in formulating effective pharmaceutical compositions.

The present therapeutic agents may be prepared with carriers that protect them against rapid elimination from the body, such as time-release formulations or coatings. Such carriers include controlled release formulations, such as, but not limited to, microencapsulated delivery systems. The active compound can be included in the pharmaceutically acceptable carrier in an amount sufficient to exert a therapeutically useful effect in the absence of undesirable side effects on the patient treated.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

The compounds of Formulae I-XV may trigger cell death by a number of different mechanisms, however, in most embodiments, the compounds of Formulae I-XV are able to induce apoptosis in unwanted, proliferative cells. The term "apoptosis" refers to the process of programmed cell death. In every person hundreds of thousands of old or damaged cells die each day by the process of apoptosis and are replaced in the ebb and flow of maintaining a constant number of living cells in the body. Old and damaged cells die in response to a signal triggered on the cell surface for the targeted cell to self destruct. Apoptosis is distinguished from other mechanisms of cell death, such as necrosis, which results in inflammation including swelling, redness, pain and tenderness. Apoptosis does not stimulate such reactions. In apoptosis, the cells shrivel up, break into pieces and the contents are quietly removed by methods that do not induce inflammation. For these reasons, it is highly desirable to induce apoptosis, rather than necrosis, in rapidly proliferating cells, such as cancer cells. However, mutations in some cancer cells confer resistance of these cells to apoptosis. The compounds of Formulae I-XV have been found to induce apoptosis even in cancer cells which, because of mutations, are otherwise resistant to apoptosis. Apoptosis can be distinguished from other treatment mechanisms by methods such as microscopy, which are known in the art.

The terms "proliferative cells," "proliferating cells," "rapidly proliferating cells," "undesirable proliferating cells," "undesirable rapidly proliferating cells," "unwanted rapidly proliferating cells," and the like, refer to cancer cells, precancer cells, and other unwanted, rapidly dividing cells in a subject.

Materials and Methods

Materials 4-[5-(4-methylphenyl)-3-(trifluoromethyl)-1H-pyrazol-1-yl]benzenesulfonamide was extracted from capsules obtained from Amerisource Health (Malvern, Pa.) with ethyl acetate followed by recrystallization from a mixture of ethyl acetate and hexane. The Cell Death Detection ELISA kit was purchased from Roche Diagnostics (Mannheim, Germany). Rabbit polyclonal antibodies against Akt and phospho-473Ser Akt were obtained from Cell Signaling Technologies (Beverly, Mass.). Mouse monoclonal anti-poly (ADPribose) polymerase (PARP) antibody was provided by Pharmingen (Sari Diego, Calif.). The PDK-1 kinase assay kit was purchased from Upstate (Lake Placid, N.Y.). Other chemical and biochemicals were obtained from Sigma-Aldrich (St. Louis, Mo.) unless otherwise mentioned. Nuclear magnetic resonance spectra ($^1$H NMR) were measured on Bruker 250 MHz. Chemical shifts (δ) are reported in parts per million (ppm) relative to TMS peak with $CDCl_3$ as solvent unless otherwise mentioned. High-resolution electrospray ionization mass spectrometry analyses were performed with a 3-Tesla Finnigan FTMS-2000 Fourier Transform mass spectrometer.

Synthesis of Chemicals

The compounds listed in Table 1 were prepared and tested as indicated below. The chemical names, proton nuclear magnetic resonance ($^1$H NMR) and high-resolution mass spectrometry (HRMS) data are summarized below. The procedures used to synthesize compounds 1-36 are described in the Examples, below.

TABLE 1

Nomenclatures, 1 H NMR (proton nuclear magnetic resonance), and HRMS (high resolution mass spectrometry) characterizations of compounds 1-36.

| Compound | Description |
|---|---|
| 1 | 4-[5-(4-(2-bromoethyl)phenyl)-3-(trifluoromethyl)-1 H-pyrazol-1-yl]benzenesulfonamide<br>$^1$H-NMR δ3.16 (t, J = 6.4, 2.0 Hz, 2 H), .3.60 (t, J = 6.4, 2.0 Hz, 2 H), 4.90 (s, 2 H), 6.75 (s, 1 H), 7.13 (d, J = 8.0 Hz, 2 H), 7.20 (d, J = 8.0 Hz, 2 H), 7.47 (d, J = 8.5 Hz, 2 H), 7.91 (d, J = 8.5 Hz, 2 H)<br>$C_{18}H_{15}BrF_3N_3O_2S$; HRMS (M + Na$^+$): theoretical mass, 495.9913; actual mass, 495.9943 |
| 2 | 4-[5-(4-(3-bromopropyl)phenyl)-3-(trifluoromethyl)-1 H-pyrazol-1-yl]benzenesulfonamide<br>$^1$H-NMR δ 2.16 (m, 2 H), 2.81 (t, J = 7.1 Hz, 2 H), 3.41 (t, J = 6.4 Hz, 2 H), .5.08 (s, 2 H), 6.76 (s, 1 H), 7.15 (d, J = 8.2 Hz, 2 H), 7.25 (d, J = 8.2 Hz, 2 H), 7.47 (d, J = 8.5 Hz, 2 H), 7.90 (d, J = 8.5 Hz, 2 H)<br>$C_{19}H_{17}BrF_3N_3O_2S$; HRMS (M + Na$^+$): theoretical mass, 510.0069; actual mass, 510.0042 |
| 3 | 4-[5-(4-(2-azidoethyl)phenyl)-3-(trifluoromethyl)-1 H-pyrazol-1-yl]benzenesulfonamide<br>$^1$H-NMR δ 2.90 (t, J = 6.8 Hz, 2 H), 3.51 (t, J = 6.8 Hz, 2 H), .5.49 (s, 2 H), 6.76 (s, 1 H), 7.17 (d, J = 8.3 Hz, 2 H), 7.24 (d, J = 8.3 Hz, 2 H), 7.42 (d, J = 8.7 Hz, 2 H), 7.85 (d, J = 8.7, 2.0 Hz, 2 H)<br>$C_{18}H_{15}F_3N_6O_2S$; HRMS (M + Na$^+$): theoretical mass, 459.0821; actual mass, 459.0817 |
| 4 | 4-[5-(4-(3-azidopropyl)phenyl)-3-(trifluoromethyl)-1 H-pyrazol-1-yl]benzenesulfonamide<br>$^1$H-NMR δ 1.83 (m, 2 H), 2.64 (t, J = 7.5 Hz, 2 H), 3.20 (t, J = 7.5 Hz, 2 H), .5.31 (br s, 2 H), 6.67 (s, 1 H), 7.07 (m, 4 H), 7.35 (dd, J = 7.5, 2.0 Hz, 2 H), 7.79 (d, J = 7.5, 2.0 Hz, 2 H)<br>$C_{19}H_{17}F_3N_6O_2S$; HRMS (M + Na$^+$): theoretical mass, 473.0978; actual mass, 473.0946 |
| 5 | 4-[5-(4-butylphenyl)-3-(trifluoromethyl)-1 H-pyrazol-1-yl]benzenesulfonamide<br>$^1$H-NMR δ 0.93 (t, J = 7.2 Hz, 3 H), 1.36 (m, 2 H), 1.64 (m, 2 H), 2.63 (t, J = 7.6 Hz, 2 H), 5.54 *sm 2 H), 6.76 (s, 1 H), 7.15 (d, J = 8.3 Hz, 2 H), 7.20 (d, J = 8.3 Hz, 2 H), 7.45 (dt, J = 8.8, 2.0 Hz, 2 H), 7.88 (dt, J = 8.8, 2.0 Hz, 2 H)<br>$C_{20}H_{20}F_3N_3O_2S$; HRMS (M + Na$^+$): theoretical mass, 446.1120; actual mass, 446.1149 |
| 6 | 4-[5-(4-t-butylphenyl)-3-(trifluoromethyl)-1 H-pyrazol-1-yl]benzenesulfonamide<br>$^1$H-NMR δ 1.33 (s, 9 H), 4.90 (s, 2 H), 6.53 (s, 1 H), 7.32 (dd, J = 9.7 Hz, 4 H), 7.42 (d, J = 8.8 Hz, 2 H), 8.02 (d, J = 8.8 Hz, 2 H)<br>$C_{20}H_{20}F_3N_3O_2S$; HRMS (M + Na$^+$): theoretical mass, 446.1120; actual mass, 446.1118 |
| 7 | 4-[5-(2-naphthalenyl)-3-(trifluoromethyl)-1 H-pyrazol-1-yl]benzenesulfonamide<br>1 H-NMR δ 5.47 (s, 2 H), 6.89 (s, 1 H), 7.18 (dd, J = 8.6, 1.6 Hz, 1 H), 7.42 (bd, J = 8.6 Hz, 2 H), 7.51-7.55 (m, 2 H), 7.78-7.83 (m, 6 H)<br>$C_{20}H_{14}F_3N_3O_2S$; HRMS (M + Na$^+$): theoretical mass, 440.0651; actual mass, 440.0657 |
| 8 | 4-[5-(3-indolyl)-3(trifluoromethyl)-1 H-pyrazol-1-yl]benzenesulfonamide<br>$^1$H-NMR δ(acetone-d$_6$)6.69 (br s, 1 H), 7.03-7.08 (m, 2 H), 7.19 (t, J = 7.2 Hz, 1 H), 7.40 (d, J = 7.8 Hz, 1 H), 7.50 (d, J = 7.8 Hz, 1 H), 7.67 (d, J = 8.7 Hz, 2 H), 7.92 (d, J = 8.7 Hz, 2 H)<br>$C_{18}H_{13}F_3N_4O_2S$; HRMS (M + Na$^+$): theoretical mass, 429.0603; actual mass, 429.0606 |
| 9 | 4-[5-4-biphenylyl)-3-(trifluoromethyl)-1 H-pyrazol-1-yl]benzensulfonamide<br>$^1$H-NMR δ 4.81 (s, 2 H), 6.75 (s, 1 H), 7.23 (d, J = 8.5 Hz, 2 H), 7.34-7.56 (m, 5 H), 7.56 (m, 4 H), 7.86 (d, J = 8.5 Hz, 2 H)<br>$C_{22}H_{16}F_3N_3O_2S$; HRMS (M + Na$^+$): theoretical mass, 466.0807; actual mass, 466.0811 |
| 10 | 4-[5-(4'-chloro[1,1'-biphenyl]-4-yl)-3-(trifluoromethyl)-1 H-pyrazol-1-yl]benzenesulfonamide<br>$^1$H-NMR δ 6.42 (s, 2 H), 6.83 (s, 1 H), 7.30 (d, J = 8.2 Hz, 2 H), 7.40-7.59 (m, 8 H), 7.92 (d, J = 8.2 Hz, 2 H)<br>$C_{22}H_{15}ClF_3N_3O_2S$; HRMS (M + Na$^+$): theoretical mass, 500.0418; actual mass, 500.0432 |
| 11 | 4-[5-(3',5'-dichloro[1,1'-biphenyl]-4-yl)-3-(trifluoromethyl)-1 H-pyrazol-1-yl]benzenesulfonamide<br>$^1$H-NMR δ 4.85 (s, 2 H), 6.82 (s, 1 H), 7.30 (d, J = 8.8 Hz, 2 H), 7.36 (s, 1 H), 7.37-7.57 (m, 6 H), 7.93 (d, J = 8.8 Hz, 2 H)<br>$C_{22}H_{14}Cl_2F_3N_3O_2S$; HRMS (M + Na$^+$): theoretical mass, 534.0028; actual mass, 534.0016 |
| 12 | 4-[5-(2',3'-dichloro[1,1'-biphenyl]-4-yl)-3-(trifluoromethyl)-1 H-pyrazol-1-yl]benzenesulfonamide<br>$^1$H-NMR δ 4.85 (s, 2 H), 6.76 (s, 1 H), 7.18-7.25 (m, 3 H), 7.35-7.49 (m, 6 H), 7.88 (d, J = 8.6 Hz, 2 H)<br>$C_{22}H_{14}Cl_2F_3N_3O_2S$; HRMS (M + Na$^+$): theoretical mass, 534.0028; actual mass, 533.9999 |
| 13 | 4-[5-(2',4',5'-trichloro[1,1'-biphenyl]-4-yl)-3(trifluoromethyl)-1 H-pyrazol-1-yl]benzenesulfonamide<br>$^1$H-NMR δ 4.86 (s, 2 H), 6.77 (s, 1 H), 7.25 (dt, J = 8.6, 2.0 Hz, 2 H), 7.37 (dt, J = 8.6, s. 0 Hz, 2 H), 7.39 (s, 1 H), 7.46 (dt, J = 8.8, 2.0 Hz, 2 H), 7.54 (s, 1 H), 7.88 (dt, J = 8.9, 1.2 Hz, 2 H)<br>$C_{22}H_{13}Cl_3F_3N_3O_2S$; HRMS (M + Na$^+$): theoretical mass, 567.9638; actual mass, 567.9679 |
| 14 | 4-[5-(4'-methyl[1,1'-biphenyl]4-yl)-3-(trifluoromethyl)-1 H-1-yl]benzenesulfonamide<br>$^1$H-NMR δ 2.32 (s, 3 H), 4.57 (s, 2 H), 6.72 (s, 1 H), 7.18-7.21 (m, 4 H), 7.39-7.52 (m, 6 H), 7.84 (d, J = 8.9 Hz, 2 H)<br>$C_{23}H_{18}F_3N_3O_2S$; HRMS (M + Na$^+$): theoretical mass, 480.0964; actual mass, 480.0961 |
| 15 | 4-[5-(4'trifluoromethyl[1,1'-biphenyl]-4-yl)-3-(trifluoromethyl)-1 H-1-yl]benzenesulfonamide<br>$^1$H-NMR δ 5.19 (s, 2 H), 6.86 (s, 1 H), 7.36 (d, J = 8.0 Hz, 2 H), 7.53 (d, J = 8.5 Hz, 2 H), 7.65 (m, 6 H), 7.92 (d, J = 8.5 Hz, 2 H)<br>$C_{23}H_{15}F_6N_3O_2S$; HRMS (M + Na$^+$): theoretical mass, 534.0681; actual mass, 534.0677 |

TABLE 1-continued

Nomenclatures, 1 H NMR (proton nuclear magnetic resonance), and HRMS (high resolution mass spectrometry) characterizations of compounds 1-36.

| Compound | Description |
|---|---|
| 16 | 4-[5-(4'-bromomethyl[1,1'-biphenyl]-4-yl)-3-(trifluoromethyl)-1 H-1-yl]benzenesulfonamide<br>$^1$H-NMR δ 3.92 (s, 2 H), 4.93 (s, 2 H), 6.66 (s, 1 H), 7.03-7.26 (m, 8 H), 7.38 (d, J = 8.6 Hz, 2 H), 7.82 (d, J = 8.6 Hz, 2 H)<br>$C_{23}H_{17}BrF_3N_3O_2S$; HRMS (M + Na$^+$): theoretical mass, 558.0069; actual mass, 558.0112 |
| 17 | 4-[5-(3',5'-dimethyl[1,1;-biphenyl]-4-yl)-3-(trifluoromethyl)-1 H-1-yl]benzenesulfonamide<br>$^1$H-NMR δ 2.40 (s, 6 H), 5.38 (br s, 2 H), 6.83 (s, 1 H), 7.05 (s, 1 H), 7.25 (m, 4 H), 7.50 (dd, J = 6.7, 1.7 Hz, 2 H), 7.59 (dd, J = 6.7, 1.7 Hz, 2 H), 7.92 (dd, J = 6.7, 1.7 Hz, 2 H)<br>$C_{24}H_{20}F_3N_3O_2S$; HRMS (M + Na$^+$): theoretical mass, 494.1120; actual mass, 494.1119 |
| 18 | 4-[5-(4'-butyl[1,1'-biphenyl]-4-yl)-3-(trifluoromethyl)-1 H-1-yl]benzenesulfonamide<br>$^1$H-NMR δ 0.96 (t, J = 7.5 Hz, 3 H), 1.41 (m, 2 H), 1.66 9m, wH), 2.68 (t, J = 7.5 Hz, 2 H), 5.20 (br s, 2 H), 6.84 (s, 1 H), 7.29 (dd, J = 8.2, 2.0 Hz, 4 H), 7.53 (dt, J = 8.2, 2.0 Hz, 4 H), 7.62 (d, J = 8.5 Hz, 2 H), 7.93 (d, J = 8.5 Hz, 2 H)<br>$C_{26}H_{24}F_3N_3O_2S$; HRMS (M + Na$^+$): theoretical mass, 522.1433; actual mass, 522.1466 |
| 19 | 4-[5-(4'-tert-buty[1,1'-biphenyl]-4-yl)-3-(trifluoromethyl)-1 H-1-yl]benzenesulfonamide<br>$^1$H-NMR δ 1.35 (s, 9 H), 4.87 (s, 2 H), 6.59 (s, 1 H), 7.44-7.57 (m, 6 H), 7.58 (d, J = 7.5 Hz, 2 H), 7.92 (d, J = 8.7 Hz, 2 H), 8.12 (d, J = 7.5 Hz, 2 H)<br>$C_{26}H_{24}F_3N_3O_2S$; HRMS (M + Na$^+$): theoretical mass, 522.1433; actual mass, 522.1401 |
| 20 | 4-[5-(4-(phenylmethyl)phenyl)-3-(trifluoromethyl)-1 H-1-yl]benzenesulfonamide<br>$^1$H-NMR δ 3.71 (s, 2 H), 4.74 (s, 2 H), 6.52 (s, 1 H), 6.91-7.11 (m, 9 H), 7.27 (d, J = 8.9 Hz, 2 H), 7.69 (d, J = 8.9 Hz, 2 H)<br>$C_{23}H_{18}F_3N_3O_2S$; HRMS (M + Na$^+$): theoretical mass, 480.0964; actual mass, 580.0938 |
| 21 | 4-[5-(9 H-fluoren-2-yl)-3-(trifluoromethyl)-1 H-1-yl]benzenesulfonamide<br>$^1$H-NMR δ 3.88 (s, 2 H), 4.64 (s, 2 H), 6.68 (s, 1 H), 7.26-7.38 (m, 4 H), 7.56 (d, J = 8.7 Hz, 2 H), 7.74-7.81 (m, 3 H), 7.90 (d, J = 8.7 Hz, 2 H)<br>$C_{23}H_{16}F_3N_3O_2S$; HRMS (M + Na$^+$): theoretical mass, 478.0807; actual mass, 478.0771 |
| 22 | 4-[5-(9-anthracenyl)-3-(trifluoromethyl)-1 H-1-yl]benzenesulfonamide<br>$^1$H-NMR δ 4.63 (s, 2 H), 6.93 (s, 1 H), 7.33 (d, J = 6.8 Hz, 2 H), 7.45-7.55 (m, 8 H), 8.04 (d, J = 6.8 Hz, 2 H), 8.60 (s, 1 H)<br>$C_{24}H_{16}F_3N_3O_2S$; HRMS (M + Na$^+$): theoretical mass, 490.0807; actual mass 490.0769 |
| 23 | 4-[5-(2-phenanthrenyl)-3-(trifluoromethyl)-1 H-1-yl]benzenesulfonamide<br>$^1$H-NMR δ (600 MHz) 4.89 (s, 2 H), 6.92 (s, 1 H), 7.37 (d, J = 8.5, 1.4 Hz, 1 H), 7.51 (d, J = 8.6 Hz, 2 H), 7.54-7.69 (m, 3 H), 7.80 (d, J = 8.8 Hz, 1 H), 7.86-7.92 (m, 4 H), 8.64 (d, J = 8.4 Hz, 2 H)<br>$C_{24}H_{16}F_3N_3O_2S$; HRMS (M + Na$^+$): theoretical mass, 490.0807; actual mass, 490.0805 |
| 24 | 4-[5-(9-phenanthrenyl)-3-(trifluoromethyl)-1 H-1-yl]benzenesulfonamide<br>$^1$H-NMR δ 4.76 (s, 2 H), 6.90 (s, 1 H), 7.43-7.84 (m, 11 H), 8.72 (t, J = 7.8 Hz, 2 H)<br>$C_{24}H_{16}F_3N_3O_2S$; HRMS (M + Na$^+$): theoretical mass, 490.0807; actual mass, 490.0833 |
| 25 | 4-[5-(2-phenanthrenyl)-3-(trifluoromethyl)-1 H-1-yl]benzenecarboxamide<br>$^1$H-NMR δ 5.75-6.05 (br d, 2 H), 7.0 (s, 1 H), 7.50 (dd, J = 8.5, 1.4 Hz, 1 H), 7.55 (d, J = 8.5 Hz, 2 H), 7.77 (m, 3 H), 7.88 (m, 3 H), 7.90 (m, 2 H), 8.72 (m, 2 H)<br>$C_{25}H_{16}F_3N_3O$; HRMS (M + Na$^+$): theoretical mass, 454.0038; actual mass, 454.1142 |
| 26 | 4-[5-(2-phenanthrenyl)-3-(trifluoromethyl)-1 H-1-yl]benzonitrile<br>$^1$H-NMR δ 6.91 (s, 1 H), 7.46 (s, 1 H), 7.50 (d, J = 2.0 Hz, 2 H), 7.63-7.79 (m, 5 H), 7.83 (d, J = 2.0 Hz, 2 H), 7.92 (m, 1 H), 8.64 (d, J = 8.4 Hz, 2 H)<br>$C_{25}H_{14}F_3N_3O$; HRMS (M + Na$^+$): theoretical mass, 436.1032; actual mass, 436.1032 |
| 27 | 4-[5-(2-phenanthrenyl)-3-(trifluoromethyl)-1 H-1-yl]-N-hydroxy-benzmidine<br>$^1$H-NMR δ 7.10 (s, 1 H), 7.34 (dd, J = 4.0, 0.9 Hz, 1 H), 7.36 (d, J = 0.9 Hz, 1 H), 7.37 (d, J = 0.9 Hz, 1 H), 7.42-7.45 (m, 3 H), 7.46 (d, J = 0.8 Hz, 1 H), 7.51-7.52 (m, 2 H), 7.53 (d, J = 0.9 Hz, 1 H), 7.57 (s, 1 H), 7.89 (s, 1 H), 7.91 (s, 1 H)<br>$C_{25}H_{17}F_3N_3O$; HRMS (M + Na$^+$): theoretical mass, 469.1220; actual mass, 469.1247 |
| 28 | 5-(2-phenanthrenyl)-3-(trifluoromethyl)-4-(1 H-tetrazol-5-ylphenyl)-1 H-pyrazole<br>$^1$H-NMR δ 6.82 (s, 1 H), 7.28 (d, J = 1.8 Hz, 1 H), 7.38 (d, J = 8.7 Hz, 2 H), 7.48-7.74 (m, 5 H), 7.74 (d, J = 2.5 Hz, 2 H), 7.95 (d, J = 8.7 Hz, 2 H), 8.47 (d, J = 8.7 Hz, 2 H)<br>$C_{25}H_{15}F_3N_6$; HRMS (M + Na$^+$): theoretical mass, 479.1202; actual mass, 479.1225 |
| 29 | 4-[5-(2-phenanthrenyl)-3-(trifluoromethyl)-1 H-pyrazol-1-yl]-benzaldehyde oxime<br>$^1$H-NMR δ 6.81 (s, 1 H), 7.27-7.30 (m, 3 H), 7.47 (d, J = 8.7 Hz, 2 H), 7.52-7.57 (m, 4 H), 76.8 (d, J = 8.8 Hz, 2 H), 7.75-7.79 (m, 2 H), 8.48-8.53 (m, 2 H)<br>$C_{25}H_{16}F_3N_3O$; HRMS (M + Na$^+$): theoretical mass, 454.1137; actual mass, 454.1106 |
| 30 | 4-[5-(2-phenanthrenyl)-3-(trifluoromethyl)-1 H-pyrazol-1-yl]-benzaldehyde hydrazone<br>$^1$H-NMR δ 6.81 (s, 1 H), 7.27-7.30 (m, 2 H), 7.33 (d, J = 1.8 Hz, 1 H), 7.42 (d, J = 8.6 Hz, 1 H), 7.53-7.55 (m, 2 H), 7.57-7.60 (m, 2 H), 7.68 (d, J = 8.9 Hz, 2 H), 7.75 (d, J = 1.7 Hz, 1 H), 7.80 (s, 1 H), 8.48-8.55 (m, 2 H)<br>$C_{25}H_{17}F_3N_4$; HRMS (M + Na$^+$): theoretical mass, 453.1297; actual mass, 453.1302 |
| 31 | 4-[5-(2-phenanthrenyl)-3-(trifluoromethyl)-1 H-pyrazol-1-yl]-phyenyl}-acetonitrile<br>$^1$H-NMR δ 3.77 (S, 2h), 6.93 (S, 1h), 7.29-7.43 (M, 4h), 7.66-7.86 (M, 6h), 8.65 (T, J = 7.0 Hz, 3 H)<br>$C_{26}H_{16}F_3N_3$; HRMS (M + Na$^+$): theoretical mass, 450.1151; actual mass, 450.1188 |
| 32 | 2-{4-[5-(2-phenanthrenyl)-3-(trifluoromethyl)-1 H-pyrazol-1-yl]-phenyl}-N-hydroxy-acetamidine<br>$^1$H-NMR δ 3.30 (s, 1 H), 3.38 (s, 1 H), 6.83 (s, 1 H), 7.20-7.41 (m, 4 H), 7.59-7.89 (m, 6 H), 8.55-8.60 (m, 3 H)<br>$C_{26}H_{19}F_3N_4O$; HRMS (M + Na$^+$): theoretical mass, 461.1580; actual mass, 461.1584 |
| 33 | 5-(2-phenanthrenyl)-3-(trifluoromethyl)-4-(1 H-tetrazol-5-ylmethylphenyl)-1 H-pyrazole<br>$^1$H-NMR δ 4.45 (s, 2 H), 7.15 (s, 1 H), 7.42 (s, 4 H), 7.53 (d, J = 6.9 Hz, 2 H), 7.66-7.76 (m, 3 H), 7.89 (d, J = 7.2 Hz, 1 H), 8.01 (m, 2 H), 8.78 (t, J = 6.9 Hz, 2 H)<br>$C_{26}H_{17}F_3N_6$; HRMS (M + Na$^+$): theoretical mass, 493.1335; actual mass, 493.1359 |
| 34 | 2-amino-N-{4-[5-(2-phenanthrenyl)-3-(trifluoromethyl)-1 H-pyrazol-1-yl]-phenyl}acetamide<br>$^1$H-NMR δ 3.48 (s, 2 H), 6.92 (s, 1 H), 7.35 (d, J = 8.8 Hz, 2 H), 7.42 (dd, J = 8.6, 1.7 Hz, 1 H), 7.62- |

TABLE 1-continued

Nomenclatures, 1 H NMR (proton nuclear magnetic resonance), and HRMS (high resolution mass spectrometry) characterizations of compounds 1-36.

| Compound | Description |
|---|---|
|  | 7.72 (m, 5 H), 7.79 (d, J = 8.8 Hz, 1 H), 7.85-7.94 (m, 2 H), 8.62 (t, J = 8.5 Hz, 2 H), 9.56 (br s 1 H) $C_{26}H_{19}F_3N_4O$; HRMS (M + Na$^+$): theoretical mass, 483.1403; actual mass, 483.1389 |
| 35 | 4-[5-(2-phenanthrenyl)-3-(trifluoromethyl)-1 H-pyrazol-1-yl]-phenyl-guanidine $^1$H-NMR δ 6.90 (s, 1 H), 7.19 (d, J = 8.7 Hz, 2 H), 7.34 (dd, J = 8.7, 2.0 Hz, 1 H), 7.39 (d, J = 8.7 Hz, 2 H), 7.61-7.67 (m, 3 H), 7.79 (d, J = 9.0 Hz, 1 H), 7.84-7.91 (m, 3 H), 8.62 (d, J = 8.3 Hz, 2 H), 9.95(s, 1 H) $C_{25}H_{18}F_3N_5$; HRMS (M + H): theoretical mass, 446.1587 (M + H); actual mass, 446.1596 (M + H) |
| 36 | 4-[5-(2-phenanthrenyl)-3-(trifluoromethyl)-1 H-pyrazol-1-yl]-phenyl-urea $^1$H-NMR δ 6.98 (s, 1 H), 7.19 (dt, J = 8.9, 2.1 Hz, 2 H), 7.34-7.42 (m, 3 H), 7.51-7.62 (m, 4 H), 7.70 (d, J = 9.0 Hz, 1 H), 7.81-7.85 (m, 2 H), 8.59-8.64 (m, 2 H) $C_{25}H_{17}F_3N_4O$; HRMS (M + Na$^+$): theoretical mass, 469.1252; actual mass, 469.1199 |

Cell Culture PC-3 (p53−/−) human androgen-non-responsive prostate cancer cells were purchased from the American Type Tissue Collection (Manassas, Va.). Cells were cultured in RPMI 1640 medium (Gibco, Grand Island, N.Y.) supplemented with 10% fetal bovine serum (FBS; Gibco) at 37° C. in a humidified incubator containing 5% $CO_2$.

Cell viability analysis The effect of 4-[5-(4-methylphenyl)-3-(trifluoromethyl)-1H-pyrazol-1-yl]benzenesulfonamide and its derivatives on PC-3 cell viability was assessed by using the MTT {[3-(4,5-dimethylthiazol-2-yl)-2,5-diphenyl-2H-tetrazolium bromide]} assay in six replicates. Cells were grown in 10% FBS-supplemented RPMI 1640 medium in 96-well, flat bottomed plates for 24 h, and were exposed to various concentrations of compounds 1-36 dissolved in DMSO (final concentration ≦0.1%) in 1% serum-containing RPMI 1640 medium for different time intervals. Controls received DMSO vehicle at a concentration equal to that in drug-treated cells. The medium was removed, replaced by 200 µl of 0.5 mg/ml of MTT in 10% FBS-containing RPMI-1640 medium, and cells were incubated in the $CO_2$ incubator at 37° C. for 2 h. Supernatants were removed from the wells, and the reduced MTT dye was solubilized in 200 µL/well DMSO. Absorbance at 570 µm was determined on a plate reader.

Cell proliferation PC-3 cells were seeded into six-well plates at 50,000 cells/well in 10% FBS-containing RPMI 1640 medium. Following a 24 h attachment period, cells were treated in triplicate with the indicated concentration of compounds 1-36 or DMSO vehicle in 10% FBS-containing RPMI-1640 medium. At different time intervals, cells were harvested by trypsinization, and numerated using a Coulter counter model Z1 D/T (Beckman Coulter, Fullerton, Calif.).

Apoptosis analysis Two methods were used to assess drug-induced apoptotic cell death: detection of DNA fragmentation by the Cell Death Detection ELISA kit (Roche Diagnostics. Mannheim, Germany) and Western blot analysis of poly-(ADP-ribose)polymerase (PARP) cleavage. The ELISA was performed according to the manufacturer's instructions, and is based on the quantitative determination of cytoplasmic histone-associated DNA fragments in the form of mononucleosomes or oligonucleosomes generated after induced apoptotic death. In brief, $4 \times 10^5$ PC-3 cells were cultured in a T-25 flask for 24 h before treatment. Cells were treated with the DMSO vehicle or the test agent at the indicated concentrations for 6-24 h, collected, and cell lysates equivalent to $2 \times 10^3$ PC-3 cells were used in the ELISA. For the PARP cleavage assay, drug-treated cells were collected 4-8 h post-treatment, washed with ice-cold PBS, and resuspended in lysis buffer containing 20 mM Tris-HCl, pH 8, 137 mM NaCl, 1 mM $CaCl_2$, 10% glycerol, 1% Nonidet P-40, 0.5% deoxycholate, 0.1% SDS, 100 µM 4-(2-aminoethyl)benzenesulfonyl fluoride, leupeptin at 10 µg/ml, and aprotinin at 10 µg/mL. Soluble cell lysates were collected after centrifugation at 10,000 g for 5 min. Equivalent amounts of proteins (60-100 µg) from each lysate were resolved in 8% SDS-polyacrylamide gels. Bands were transferred to nitrocellulose membranes, and analyzed by immunoblotting with anti-PARP antibody.

Immunoblotting. The general procedure for the Western blot analysis of Akt and phospho-Akt is described as follows. Cells were washed in PBS, resuspended in SDS sample buffer sonicated by an ultrasonic sonicator for 5 sec, and boiled for 5 min. After brief centrifugation, equivalent protein concentrations from the soluble fractions were resolved in 10% SDS-polyacrylamide gels on a Minigel apparatus, and transferred to a nitrocellulose membrane using a semi-dry transfer cell. The transblotted membrane was washed three times with TBS containing 0.05% Tween 20 (TBST). After blocking with TBST containing 5% nonfat milk for 60 min., the membrane was incubated with the primary antibody at 1:1,000 dilution in TBST-5% low fat milk at 4° C. for 12 h, and was then washed three times with TBST. The membrane was probed with goat anti-rabbit IgG-HRP conjugates (1:1,000) for 1 h at room temperature, and was washed with TBST three times. The immunoblots were visualized by enhanced chemiluminescence.

PDK-1 kinase activity This in vitro assay was performed using a PDK-1 kinase assay kit (Upstate, Lake Placid, N.Y.) according to the vendor's instructions. This cell-free assay is based on the ability of recombinant PDK-1, in the presence of DMSO vehicle or the test agent, to activate its downstream kinase serum- and glucocorticoid-regulated kinase (SGK.) which, in turn, phosphorylates the Akt/SGK-specific peptide substrate RPRAATF with [γ-$^{32}$P]-ATP. The [$^{32}$P]-phosphorylated peptide substrate was then separated from the residual [γ-$^{32}$P]-ATP using P81 phosphocellulose paper and quantitated by a scintillation counter after three washes with 0.75% phosphoric acid. The reported values represent the means of two independent determinations.

Immunoprecipitated Akt kinase assay Akt immunoprecipitation was carried out according to a modified, published procedure. PC-3 cells were treated with DMSO vehicle or the test agents at the indicated concentrations for 2 h and then lysed at 4° C. for 1 h in buffer A containing 50 mM Tris-HCl, pH 7.5, 1% Triton X-100, 1 mM EDTA, 1 mM EGTA, 50 mM sodium fluoride, 10 mM sodium β-glycerophosphate. 0.1% 2-mercaptoethanol, 0.1 mM phenylmethylsiilfonyl fluoride, and 1 µg/mL each of aprotinin, pepstatin, and leupeptin. Cell lysates were centrifuged at 10,000 g for 5 min, and the supernatant was treated with anti-Akt at 4° C. for 60 min., followed by protein G-agarose beads for additional 60 min. The immunoprecipitate was used to analyze Akt kinase activity by using the Akt/SGK-specific peptide substrate RPRAATF as described above. Values represented the means of two independent determinations.

Statistical analysis Each experiment was performed in triplicate, unless otherwise mentioned. All experiments were carried out at least two times on different occasions. Where appropriate, the data are presented as the mean±95% confidence interval.

The structure and potency in inhibiting PDK-1 kinase activity and PC-3 cell growth of 24 representative derivatives are summarized in Table 2.

TABLE 2

Structures and potency for inhibiting recombinant PDK-1 kinase activity and for inducing apoptotic death in PC-3 cells for 4-[5-(4-methylphenyl)-3-(trifluoromethyl)-1H-pyrazol-1-yl] benzenesulfonamide and compounds 37-60 (1-24)

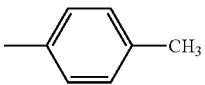

| Number | Ar | IC$_{50}$ (μM) PDK-1 | PC-3 |
|---|---|---|---|
| Comparative Compound | 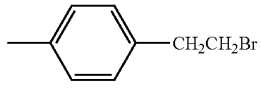 | 48 | 30 |
| 37 | 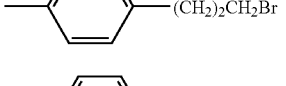 | 42 | 18 |
| 38 | 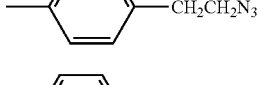 | 38 | 17 |
| 39 | 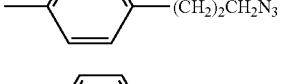 | 32 | 17 |
| 40 | 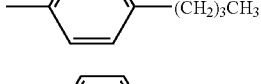 | 34 | 18 |
| 41 | 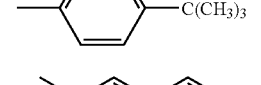 | 20 | 9 |
| 42 | 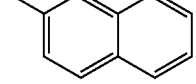 | 34 | 18 |
| 43 | 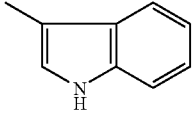 | 24 | 11 |
| 44 | 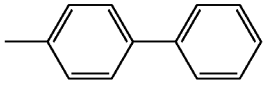 | 65 | 31 |
| 45 | 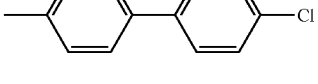 | 21 | 11 |
| 46 | 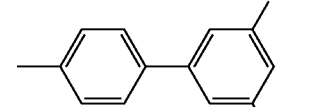 | 22 | 9 |
| 47 | 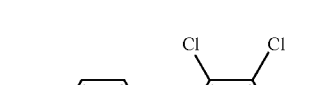 | 18 | 10 |
| 48 | 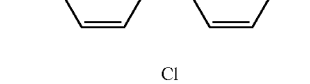 | 23 | 10 |
| 49 | 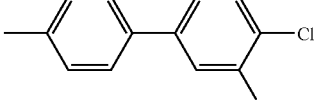 | 9 | 5 |
| 50 | 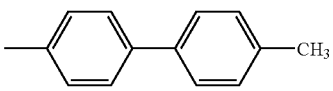 | 15 | 8 |
| 51 | 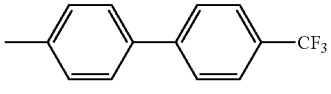 | 18 | 8 |
| 52 | | 20 | 11 |

TABLE 2-continued

Structures and potency for inhibiting recombinant PDK-1 kinase activity and for inducing apoptotic death in PC-3 cells for 4-[5-(4-methylphenyl)-3-(trifluoromethyl)-1H-pyrazol-1-yl] benzenesulfonamide and compounds 37-60 (1-24)

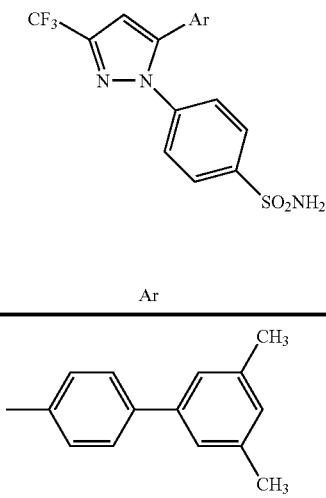

| Number | Ar | IC₅₀ (μM) PDK-1 | PC-3 |
|---|---|---|---|
| 53 | 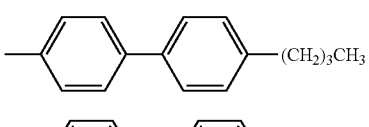 | 17 | 9 |
| 54 | 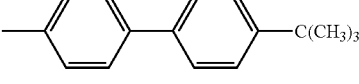 | 32 | 15 |
| 55 | 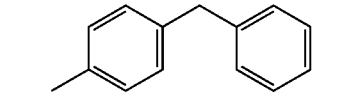 | 32 | 15 |
| 56 | 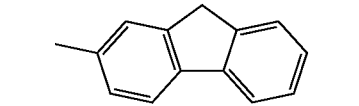 | 15 | 8 |
| 57 | 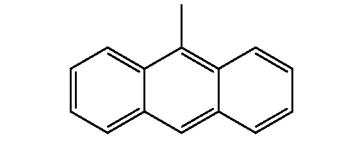 | 16 | 9 |
| 58 |  | 12 | 7 |
| 59 | 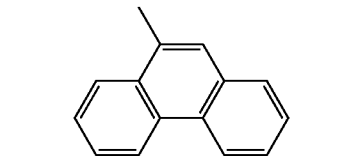 | 9 | 5 |
| 60 |  | 42 | 23 |

These compounds, except the indole derivative 44, showed improved PDK-1 inhibitory and anti-proliferative activities vis-à-vis 4-[5-(4-methylphenyl)-3-(trifluoromethyl)-1H-pyrazol-1-yl] benzenesulfonamide. Additionally, none of these compounds displayed measurable COX-2 inhibitory activity (data not shown). A general increase in PDK-1 inhibitory activity was noted with increasing bulkiness of the aromatic ring, i.e., tricyclic aromatic rings (57-59)>substituted biphenyl (45-55)>substituted phenyl (37-42). These data suggested that the aromatic system bound to a large, hydrophobic region of the enzyme pocket. Among the 24 analogues examined, compound 59 represented the optimal derivative with IC₅₀ values of 9 μM and 5 μM for inhibiting PDK-1 activity and PC-3 cell viability, respectively, as reported in Table 2. These IC₅₀ values corresponded to a five- to six-fold improvement over the activities of 4-[5-(4-methylphenyl)-3-(trifluoromethyl)-1H-pyrazol-1-yl] benzenesulfonamide (48 μM and 30 μM, respectively). However, compound 60 exhibited a decrease, compared with compound 59 in PDK-1 inhibitory activity, which might be attributable to steric hindrance imposed by an unfavorable orientation of the tricyclic aromatic ring.

There existed a correlation between PDK-1 and PC-3 growth inhibition potency in all compounds examined, suggesting the mechanistic relevance of PDK-1 inhibition to the anti-proliferative effect. Overall, the IC₅₀ value for inhibiting PC-3 cell proliferation was approximately one half of that of PDK-1 inhibition. This discrepancy might arise from a mechanistic synergy between PDK-1 inhibition and concomitant Akt dephosphorylation by protein phosphatase 2A (PP2A) in Aug-treated cells, resulting in augmented Akt deactivation. To examine this premise, PC-3 cells were treated with different concentrations of compound 59 for 2 h, and the consequent effect on AM was assessed by two independent assays: immunoprecipitated Akt kinase activity and Akt phosphorylation status. Both assays gave consistent results.

According to the kinase assay, the IC₅₀ of compound 59 for inhibiting intracellular Akt activation was 5 μM. Neither compound 59 nor other the other compounds displayed a direct inhibitory effect on immunoprecipitated Akt activity. Meanwhile, Western blot analysis shows that treatment of PC-3 cells with compound 59 at 5 μM and above led to significant Akt dephosphorylation.

The inhibition of PDK-1/Akt signaling led to apoptotic death in PC-3 cells in 1% FBS-containing RPMI 1640 medium in a dose-dependent manner, as was evidenced by DNA fragmentation and PARP cleavage. The dose of compound 59 required to induce 50% PC-3 cell death at 24 h was 5 μM. The IC₅₀ values for compound 59 to induce PC-3 cell death was consistent with that of inhibiting Akt activation in drug-treated cells. Furthermore, the effect of compound 59 on PC-3 cell proliferation was examined in 10% FBS-supplemented RPMI 1640 medium. Compound 59 at 1 μM showed substantial anti-proliferative activity. Together, these data clearly indicated the in vitro efficacy of compound 59 in PC-3 growth inhibition.

The modeling showed that compound 59 was docked into the ATP-binding domain that is located within a deep cleft between the two lobes of PDK-1. Although compound 59 competed with ATP for binding, the mode of binding for compound 59 was found to be somewhat different from that of ATP. While the benzenesulfonamide moiety occupied the adenine-binding motif, the planar pyrazole moiety was perpendicular to the ribose ring. This arrangement positioned the adjacent phenanthrene ring behind the trisphosphate-binding pocket. The phenanthrene ring formed hydrophobic interactions with an apolar region formed by residues 88-96 encompassing part of two adjacent β sheets joined by a glycine-rich loop.

Structures of twelve representative derivatives, their potency against PDK-1, and their ability to cause apoptotic death in PC-3 cells are summarized in Table 3.

TABLE 3

Structures and potency for inhibiting recombinant PDK-1 kinase activity and for inducing apoptotic death in PC-3 cells for compounds 25-36. The general structures of these compounds is shown at top.

| Number | R | IC₅₀ (μM) PDK-1 | IC₅₀ (μM) PC-3 |
|---|---|---|---|
| 61 | —CONH₂ | 12 | 7 |
| 62 | —CN | 45 | 30 |
| 63 | (N-OH, CH₃, NH₂ group) | 40 | 25 |
| 64 | (methyl-tetrazole) | 52 | 32 |
| 65 | (N-OH, CH₃, H group) | 25 | 14 |
| 66 | —CH=N—NH₂ | 16 | 10 |
| 67 | —CH₂CN | 42 | 25 |
| 68 | (N-OH, ethyl, NH₂ group) | 15 | 8 |
| 69 | (—H₂C-tetrazole) | 45 | 27 |
| 70 | —NHC(O)CH₂NH₂ | 5 | 5 |
| 71 | —NHC(=NH)NH₂ | 2 | 3 |
| 72 | —NHC(O)NH₂ | 40 | 24 |

Among these derivatives, compound 70 and 71 exhibited IC₅₀ values for PDK-1 inhibition of 5 μM and 2 μM, respectively, which represented two- and five-fold increases in potency over compound 59. Compounds 70 and 71 contained side chains of 2-aminoacetamide (—NHC(O)CH₂NH₂,) and guanidine (—NHC(=NH)NH₂), respectively. Like compound 59, they exhibited no appreciable direct inhibition on immunoprecipitated Akt kinase activity, nor was any measurable COX-2 inhibitory activity detected at concentrations up to 50 μM. Exposure of PC-3 cells to either agent, even at 1 μM, resulted in a substantial decrease in the phospho-Akt level. This improvement in potency reflected a strengthening of the hydrogen bonding in the protein-ligand interactions for these derivatives. This premise was supported by the modeled docking of compound 71 into the ATP-binding site. The guanidino group of compound 71 resembled the partial structure of ATP's purine ring, which allowed the formation of hydrogen bonds with Ser160 and Ala162 as depicted by the docking model.

Figure 1:
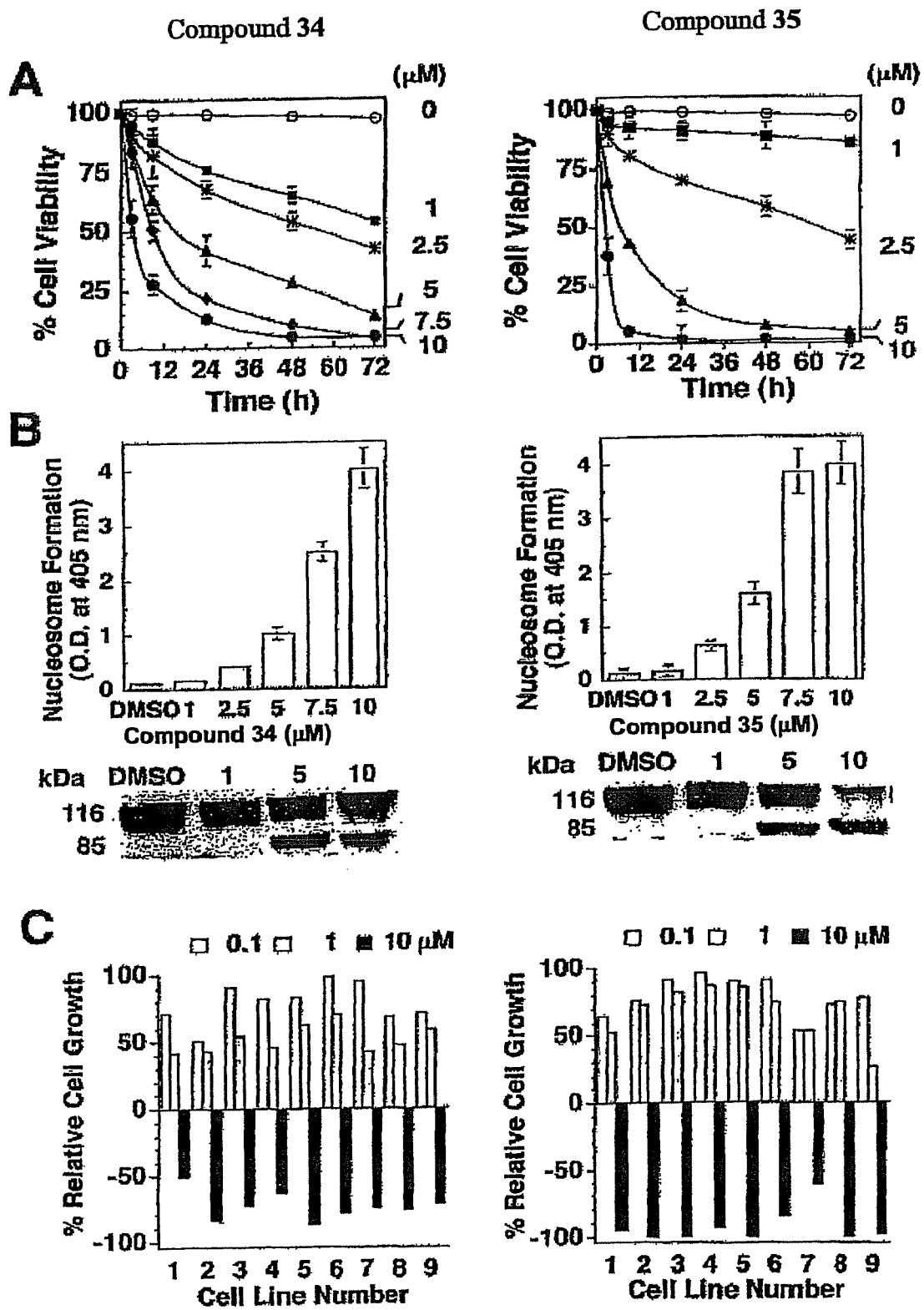

Cellular effects of PDK-1/Akt signaling inhibitors Both compound 34/70 and compound 35/71 induced apoptotic death in PC-3 cells in 1% FBS-containing medium in a dose-dependent manner, as was demonstrated by DNA fragmentation and PARP cleavage. These agents exhibited higher potency than compound 59 in apoptosis induction at concentrations greater than 2.5 μM. Moreover, these derivatives were submitted to the Developmental Therapeutic Program (DTP) at the National Cancer Institute (NCI) for screening against sixty human tumor cell lines, representing leukemia, melanoma, and cancers of the lung, colon, brain, ovary, breast, prostate, and kidney. Dose-response data of one representative cell line from each class of tumor cells after two-day exposure in 5% FBS-containing medium are shown in FIG. 1C, which include: 1, RPMI-8226 leukemia cells; 2, NCI-H322M non-small cell lung cancer cells; 3, HT29 colon cancer cells; 4, U251 CNS cancer cells; 5, SK-MEL-28 melanoma cancer cells; 6, SK-OV-3 ovarian cancer cells; 7, RXF 393 renal cancer cells; 8, PC-3 prostate cancer cells; 9, MDA- MB-231 breast cancer cells. Many of these cell lines were responsive to the growth inhibitory effect of both agents at concentrations as low as 0.1 µM In the sixty cell line assay, three dose response parameters for each cell line were calculated based on growth inhibition curves. These parameters include GI50 (concentration resulting in 50% growth inhibition), TGI (concentration resulting in total growth inhibition), and LC50 (concentration resulting in a 50% reduction in the measured protein level at the end of drug treatment as compared to that at the beginning). The means of these parameters among the sixty different cell lines for compounds 70 and 71 after two-day treatment were as follows, respectively, GI50: 1.1 and 1.2 µM; TGI: 3.2 and 2.9 µM; LC50: 24 and 8.5 µM. These data clearly demonstrate the in vitro efficacy of compounds 70 and 71. Both agents were able to completely suppress cell growth in a diverse range of tumor cell lines at the 3-5 µM therapeutic range.

In light of the conserved role of PDK-1/Akt signaling in cancer cell survival and proliferation, this pathway represents a therapeutically relevant target for developing orally bioavailable, small-molecule inhibitors.

In silico docking of compound 59 into the ATP-binding pocket showed that the molecule was anchored into the ATP binding domain, in part, through hydrogen bonding between the sulfonamide and the amide of Ala162. Ala162 has also been reported to play a key role in anchoring other ligands such as ATP[17] and UCN-01 to PDK-1. Together, these data suggest that the sulfonamide moiety of compound 59 might be amenable to alterations for optimizing potency.

Accordingly, replacement of the sulfonamide function with 2-aminoacetamide (—NHC(O)CH$_2$NH$_2$) and guanidine [—NHC(=NH)NH$_2$] led to compounds 70 and 71, respectively, both of which exhibited improved PDK-1 inhibition with IC$_{50}$ values of 5 and 2 µM, respectively. Docking of compound 71 into the ATP binding site revealed the existence of an additional hydrogen bond between the guanidine moiety and the backbone-oxygen of Ser160, suggesting that the enhancement in potency might be attributable to an increase in hydrogen bonding. The effect of these side chains on ligand binding, however, is subtle, as illustrated by the structure-activity relationship summarized in Table 3.

The high potency of compounds 70 and 71 in PDK-1 inhibition was reflected in their abilities to effectively block Akt activation and to induce apoptotic cell death in PC-3 cells at low µM concentrations (FIG. 1A, B). More importantly, due to the conserved role of PDK-1/Akt signaling in cell proliferation and survival, these agents were potent in inhibiting cell growth in serum-containing medium in all 60 human tumor cell lines examined, with mean GI50 (50% cell growth inhibition) values of 1.2 µM and 1.3 µM, respectively, arid TGI (total growth inhibition) values of 3.2 µM and 2.9 µM, respectively. Our preliminary animal studies have shown that these compounds can be orally absorbed, can generate average serum concentrations several-fold higher than TGI, and more importantly, incur little toxicity to the animals after daily oral administration for one month (data not shown).

General Synthetic Procedures for Compounds 37-60

All chemical reagent and organic solvents were purchased from Aldrich (St. Louis, Mo.) unless otherwise mentioned. Compounds 1-24 were synthesized according to a two-step general procedure described in Scheme 1, in which Ar represents the respective aromatic ring structures.

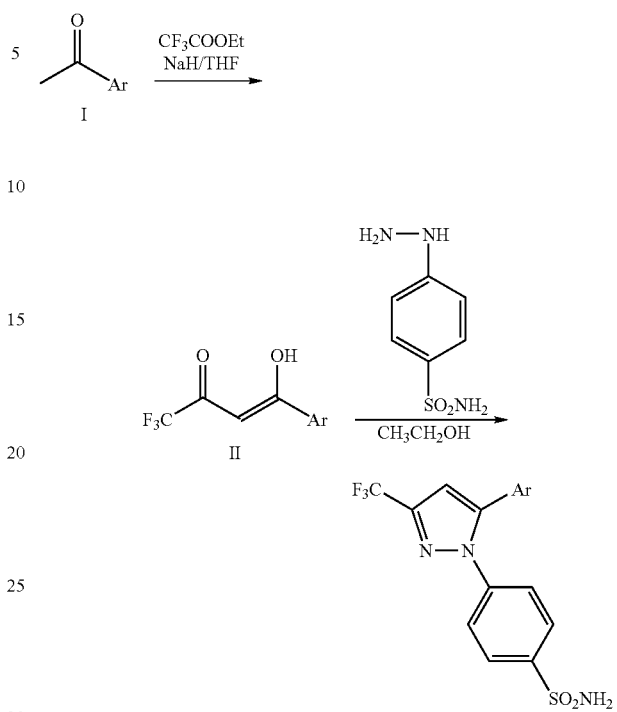

Scheme 1

Compound 59 is used here as an example to illustrate the synthesis of the group of compounds (Scheme 2). Other compounds followed the same procedures via precursors and the respective intermediates with different aromatic ring structures (compounds I and II).

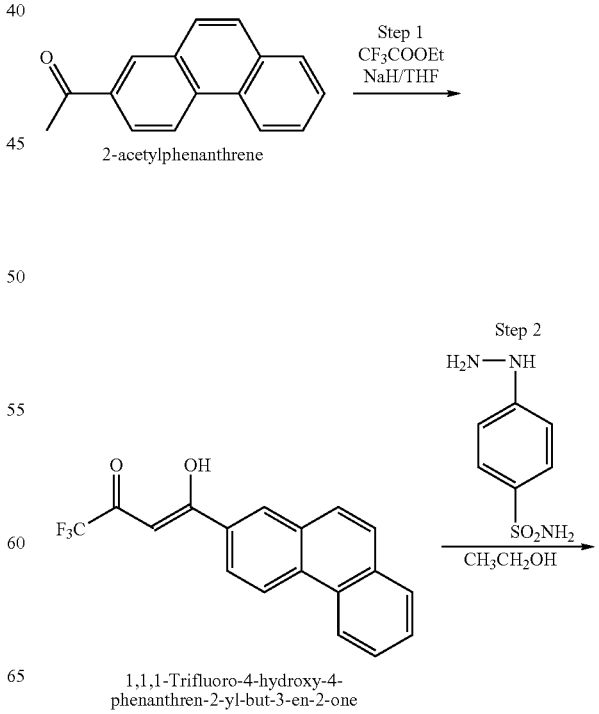

Scheme 2

2-acetylphenanthrene 1,1,1-Trifluoro-4-hydroxy-4-phenanthren-2-yl-but-3-en-2-one

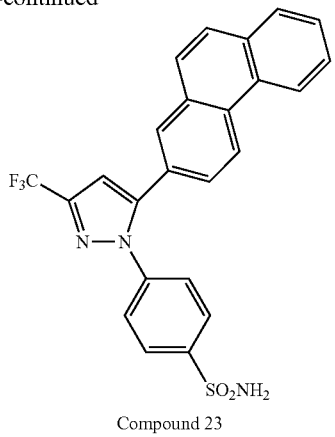

Compound 23

EXAMPLE 1

Synthesis of the 1,1,1-Trifluoro-4-hydroxy-4-phenanthren-2-yl-but-3-en-2-one Precursor (step 1). To a suspension of sodium hydride (NaH; 0.13 g, 5.4 mmol) in 5 mL of anhydrous tetrahydrofuran (THF) was added ethyl trifluoracetate ($CF_3COOEt$; 0.64 g, 4.5 mmol) under argon. After stirring at 25° C. for 10 minutes, 2-acetylphenanthrene (1 g, 4.5 mmol) in 5 mL of THF was added dropwise to the solution. The mixture became clear and orange-hued within 30 minutes, and after stirring for an additional 2 hours, was concentrated under vacuum. The residue was suspended in water, and extracted with ethyl acetate (15 mL) twice. The organic phase was separated, dried over sodium sulfate, and concentrated to dryness under vacuum to give the product (yellow solid; 1.29 g, 90% yield). The product was used directly without further purification.

EXAMPLE 2

Synthesis of Compound 59 (step 2). 4-Hydrazinobenzene-1-sulfonamide hydrochloride (1.1 g; 4.9 mmol) was added to a stirred solution of 1,1,1,-trifluoro-4-hydroxy-4-phenanthren-2-yl-but-3-en-2-one (1.29 g, 4.1 mmol) in 40 mL of ethanol. The mixture was refluxed for 12 hours, cooled to room temperature, and concentrated to dryness under vacuum. The residue was dissolved in ethyl acetate, and washed with water. The organic layer was dried over sodium sulfate, and concentrated under vacuum. The crude product was purified by silica gel flash chromatography to yield 59 (1.52 g, 80% yield).

EXAMPLES 3-14

Figure 2:
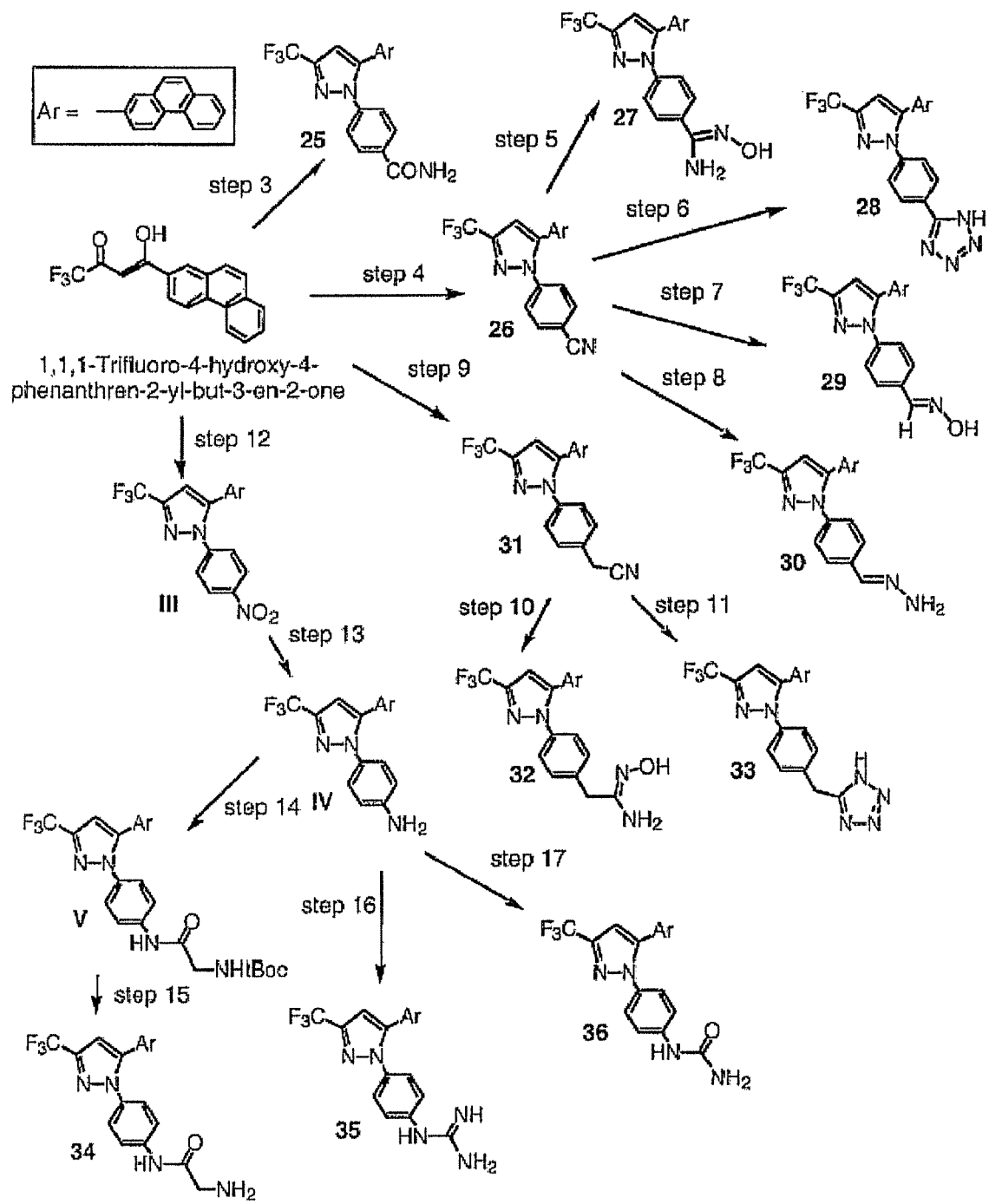

Syntheses of Compounds 61-72 Compounds 61-72 (25-36) were synthesized using 1,1,1-trifluoro-4-hydroxy-4-phenanthren-2-yl-but-3-en-2-one, product of the aforementioned step 1, as a common precursor (Scheme 3, FIG. 2).

EXAMPLE 3

4-[5-(2-Phenanthracenyl)-3-(trifluoromethyl)-1H-pyrazol-1-yl]-benzenecarboxamide (61) (step 3). (4-Carbamoylphenyl)-hydrazine hydrochloride (0.92 g, 4.9 mmol) was added to a stirred solution of 1,1,1-trifluoro-4-hydroxy-4-phenanthren-2-yl-but-3-en-2-one (1.29 g, 4.1 mmol) in 40 mL of ethanol at 25° C. The mixture was refluxed for 12 hours, cooled to room temperature and concentrated to dryness under vacuum. The residue was dissolved in ethyl acetate, and washed with water. The organic layer was dried over sodium sulfate, and concentrated under vacuum. The crude product was purified by silica gel flash chromatography (ethyl acetate-hexane, 1:1), —yielding 61 (1 g, 60% yield).

EXAMPLE 4

4-[5-(2-Phenanthrenyl)-3-(trifluoromethyl)-1H-pyrazol-1-yl]-benzonitrile (62) (step 4). To a stirred solution of 1,1,1-trifluoro-4-hydroxy-4-phenanthren-2-yl-but-3-en-2-one (2.45 g, 7.7 mmol) in 60 mL of ethanol was added 4-cyanophenylhydrazine hydrochloride (2.53 g, 15 mmol) at 25° C. The mixture was stirred under reflux for 12 hours, cooled to room temperature and concentrated to dryness under vacuum. The residue was dissolved in methylene chloride, and washed with water. The organic layer was dried over sodium sulfate, and concentrated under vacuum. The crude product was purified by silica gel flash chromatography (ethyl-acetate-hexane, 1:4) to afford 62 (2.7 g, 85% yield).

EXAMPLE 5

4-[5-(2-Phenanthrenyl)-3-(trifluoromethyl)-1H-pyrazol-1-yl]-N-hydroxybenzamidine (63) (step 5). Hydroxylamine hydrochloride (25 mg, 0.36 mmol) was added to a suspension of Na metal (8.3 mg, 0.36 mmol) in methanol (3 mL). The mixture was stirred at room temperature for 10 minutes. and compound 62 (1224 mg, 0.3 mmol) was added. The mixture was refluxed for 2 hours, then stirred at 25° C. for an additional 16 hours, and concentrated under vacuum. The residue was purified by silica gel flash chromatography (ethyl acetate-hexane, 1:4 to 1:1) to give 63 (120 mg, 76% yield).

EXAMPLE 6

5-(2-Phenanthrenyl)-3-(trifluoromethyl)-4-(1H-tetrazol-5-ylphenyl)-1H-pyrazole (64) (step 6). A mixture containing compound 62 (125 mg, 0.3 mmol), $NH_4Cl$ (123.7 mg), and $NaN_3$ (58.5 mg, 0.9 mmol) in 5 mL of 10% HCl was added, and extracted with 20 mL of methylene chloride, twice. The organic phase was dried over sodium sulfate, and concentrated to dryness under vacuum. The crude product was purified by silica gel flash chromatography (ethyl acetate-hexane 1:4) to give 64 (96 mg, 70% yield).

EXAMPLE 7

4-5-[-(2-Phenanthrenyl)-3-(trifluoromethyl)-1H-pyraxol-1-yl]-benzaldehyde oxime (65) (step 7). DIBAL-H (3.1 mL, 3.1 mmol, 1.0 M in hexane) was added dropwise to a solution of compound 62 (0.417 g, 1.1 mmol) in 5 mL THF at −40° C. The mixture was stirred for 8 hours, poured into 5 mL of 10% acetic acid, and stirred for 30 minutes. The organic layer was dried over sodium sulfate, and concentrated to dryness under vacuum. The crude product was purified by silica gel flash chromatography (ethyl acetate-hexane, 1:4) to give an aldehyde intermediate (141 mg, 0.34 mmol) that was immediately added to a solution containing hydroxylamide hydrochloride (211 mg) and $K_2CO_3$ in 5 mL of ethanol. The mixture was stirred under reflux for 16 hours. After removal of solvent, the residue was extracted with $CH_2Cl_2$ and washed with water.

EXAMPLE 8

4-[5-(2-Phenanthrenyl)-3-(trifluoromethyl)-1H-pyrazol-1-yl]-benzaldehyde hydrazone (66) (step 8). Compound 66

(124 mg, 85% yield) was synthesized in the same manner as 65 except that hydrazine monohydrate (153 mg, 3.1 mmol) was used instead of hydroxylamine hydrochloride.

EXAMPLE 9

{4-[5-(2-Phenanthrenyl)-3-(trifluoromethyl)-1H-pyrazol-1-yl]-phenyl}-acetonitrile (67) (step 9). (a) Preparation of (4-Hydrazinophenyl)acetonitrile hydrochloride. A solution of sodium nitrite (3.15 g, 45.7 mmol) in water (20 mL) was added dropwise to a cooled (−15° C.), stirred suspension of 4-aminobenzonitrile (5 g, 42.3 mmol) in a concentrated hydrogen chloride solution (55 mL) at such a rate as to maintain a temperature below −10° C. After the addition was finished, the reaction mixture was quickly filtered to remove solids, and the filtrate was added in portions to a cooled (−20° C.), stirred solution of $SnCl_2.2H_2O$ (47.7 g, 0.21 mol) in a concentrated hydrogen chloride solution (37 mL) at such a rate as to keep the temperature below −10° C. After stirring the solution for an additional 15 minutes, the solid was collected, washed with diethyl ether (4×25 mL), and dried to give (4-hydrazinophenyl)acetonitrile hydrochloride (5.6 g, 78%). (b) Compound 67. A mixture of (4-hydrazinophenyl)acetonitrile hydrochloride (0.32 g, 1 mmol) and 1,1,1-trifluoro-4-hydroxy-4-phenanthren-2-yl-but-3-en-2-one (0.18 g, 1.1 mmol) in ethanol (20 mL) was stirred under reflux for 24 hours, cooled to room temperature, concentrated to dryness under vacuum, and dissolved in ethyl acetate. The organic layer was dried over magnesium sulfate, and concentrated to dryness under vacuum. The crude product was purified by silica gel column chromatography (hexane-ethyl acetate, 2:1) to give compound 67 (0.35 g, 81% yield).

EXAMPLE 10

2-{4-[5-(2-Phenanthrenyl)-3-(trifluoromethyl)-1H-pyrazol-1-yl]-phenyl}-N-hydroxy-acetamidine (68) (step 10). A solution of compound 67 (0.43 g, 1 mmol) and hydroxyamine hydrochloride (0.075 g, 1.1 mmol) in ethanol (10 mL) was stirred under reflux for 8 hours, and concentrated to dryness under vacuum. The residue was dissolved in water, brought to pH 8-9 by addition of saturated $NaHCO_3$ solution, and extracted with ethyl acetate. The organic layer was dried over magnesium sulfate, and concentrated to dryness under vacuum. The crude product was re-crystallized in diethyl ether-hexane to give compound 68 (0.32 g, 71% yield).

EXAMPLE 11

5-(2-Phenanthrenyl)-3-(trifluoromethyl)-4-(1H-tetrazol-5-ylmethylphenyl)-1H-pyrazole (69) (step 11). A mixture containing compound 67 (0.43 g, 1 mmol), sodium azide (0.08 g, 1.2 mmol), and triethylamine hydrochloride (0.12 g, 1.2 mmol) in toluene (5 mL) was stirred at 100 C for 5 hours, cooled to room temperature, and extracted with water (10 mL). To the aqueous phase was added dropwise a 36% hydrogen chloride solution to salt out the resulting tetrazole 69. After filtration, the solid was dried under vacuum, yielding compound 33 (0.39 g, 84% yield).

EXAMPLES 12-14

1-(4-Nitrophenyl)-5-phenyl-3-(trifluoromethyl)-1H-pyrazole (III) (step 12). To a solution of 1,1,1-trifluoro-4-hydroxy-4-phenanthren-2-yl-but-3-en-2-one (1.29 g, 4.1 mmol) in 40 mL of ethanol was added 4-nitrophenylhydrazine hydrochloride (0.93 g, 4.9 mmol) under stirring, refluxed for 1 hour, cooled to room temperature, and concentrated to dryness under vacuum. The residue was dissolved in ethyl acetate, and washed with water. The organic phase was dried over magnesium sulfate, and concentrated to dryness under vacuum. The crude product was purified by silica gel column chromatography to afford compound III (0.88 g, 50% yield).

4-[5-(2-Phenanthrenyl)-3-(trifluoromethyl)-1H-pyrozol-1-yl]phenylamine (IV) (step 13). To a solution of compound III (0.88 g, 2 mmol) in 20 mL ethanol was added platinum oxide (27 mg, 0.12 mmol), stirred under $H_2$ at 55 psi for 12 hours, filtered to remove the catalyst, and concentrated to dryness under vacuum. The crude product was purified by silica gel chromatography to yield compound IV (0.57 g, 70% yield).

EXAMPLE 12

2-Amino-N-{4-[5-(2-phenanthrenyl)-3-(trifluoromethyl)-1H-pyrazol-1-yl]-phenyl}-acetamide (70) (steps 14 and 15). To a solution of t-butyloxycarbonyl (tBOC)-glycine (0.25 g, 1.4 mmol) and compound IV (0.57 g, 1.4 mmol) in 10 mL of tetrahydrofuran was added 1-[3-(dimethylamino)propyl]-3-ethylcarbodiimide hydrochloride (0.41 g, 2.1 mmol), stirred at 25° C. for 12 hours, and concentrated to dryness under vacuum in a rotary evaporator. The residue was suspended in water, and the product was extracted with ethyl acetate. The organic phase was dried over magnesium sulfate, and concentrated to dryness under vacuum to give compound V (0.67 g, 85% yield). Compound V (0.67 g, 1.2 mmol) was dissolved in 8 mL of ethyl acetate containing 0.7 mL of concentrated HCl solution, stirred at room temperature for 2 hours, and concentrated to dryness under vacuum. The crude product was purified y silica gel column chromatography to yield compound 70 as a white powder (0.49 g, 90%).

EXAMPLE 13

4-[5-(2-Phenanthrenyl)-3-(trifluoromethyl)-1H-pyrazol-1-yl]-phenyl-guanidine (71) (step 16). To a solution of compound IV (0.57 g, 1.4 mmol) in 7 mL of ethanol was added cyanamide (89 mg, 2.1 mmol) and 1.5 mL of 1N HCl. The mixture was refluxed for 24 hours, and concentrated to dryness under vacuum. The product was purified by silica gel column chromatography to give compound 71 as a white solid (0.25 g, 40% yield).

EXAMPLE 14

4-[5-(2-Phenanthrenyl)-3-(trifluoromethyl)-1H-pyrazol-1-yl]phenyl urea (72) (step 17). Into a 250 mL round bottom flask containing acetic acid (50 mL), water (12 mL), and ethanol (20 mL) was added compound IV (2.25 g, 5.6 mmol), followed by sodium isocyanate (0.74 g, 11.2 mmol). The reaction was stirred for 1.5 hours, and then neutralized with the addition of 1 N sodium hydroxide followed by sodium hydroxide pellets until the pH had changed to 7.0. The product was separated and then washed with 100 mL of water, dried with magnesium sulfate, and then solvent was removed to obtain the crude product. Purification was performed by silica gel chromatography with (hexane-ethyl acetate, 3:2 to hexane-acetone, 1:3) to afford compound 72.

EXAMPLE 15

Preparation of Additional Compounds The compounds in Table 4 were prepared using the methods of the Examples above.

TABLE 4

Additional Compounds

| Compound | R | Nomenclature |
|---|---|---|
| 73 | -NHC(O)CH₃ on phenyl with SO₂NH₂ | 4-(5-Phenanthren-2-yl-3-trifluoromethyl-pyrazol-1-yl)-N-(4-sulfamoyl-phenyl)-benzamide |
| 74 | -N(H)C(O)- methyl amide linked to benzene-SO₂NH₂ | N-[4-(5-Phenanthren-2-yl-3-trifluoromethyl-pyrazol-1-yl)-phenyl]-4-sulfamoyl-benzamide |
| 75 | methylamide-CH₂-NH-C(=NH)NH₂ | 2-Guanidino-N-[4-(5-phenanthren-2-yl-3-trifluoromethyl-pyrazol-1-yl)-phenyl]-acetamide |
| 76 | methylamino-CH₂-C(O)NH₂ | 2-[4-(5-Phenanthren-2-yl-3-trifluoromethyl-pyrazol-1-yl)-phenylamino]-acetamide |
| 77 | methylamide-CH₂-NH-C(O)-phenyl | N-{[4-(5-Phenanthren-2-yl-3-trifluoromethyl-pyrazol-1-yl)-phenylcarbamoyl]-methyl}-benzamide |

EXAMPLE 16

Screening of compounds 70 and 71 against several cancer cell lines The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 µL at plating densities ranging from 5,000 to 40,000 cells/well depending on the doubling time of individual cell lines. After cell inoculation, the microtiter plates are incubated at 37° C., 5% $CO_2$, 95% air and 100% relative humidity for 24 h prior to addition of experimental drugs.

After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 µg/ml gentamicin. Additional four, 10-fold or ½ log serial dilutions are made to provide a total of five drug concentrations plus control. Aliquots of 100 µl of these different drug dilutions are added to the appropriate microtiter wells already containing 100 µl of medium, resulting in the required final drug concentrations.

Following drug addition, the plates are incubated for an additional 48 h at 37° C., 5% $CO_2$, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

[(Ti−Tz)/(C−Tz)]×100 for concentrations for which Ti>/=Tz

[(Ti−Tz)/Tz]×100 for concentrations for which Ti<Tz

Three dose response parameters are calculated for each experimental agent. Growth inhibition of 50% ($GI_{50}$) is calculated from [(Ti−Tz)/(C−Tz)]×100=50, which is the drug concentration resulting in a 50% reduction in the net protein increase (as measured by SRB staining) in control cells during the drug incubation. The drug concentration resulting in total growth inhibition (TGI) is calculated from Ti=Tz. The $LC_{50}$ (concentration of drug resulting in a 50% reduction in the measured protein at the end of the drug treatment as compared to that at the beginning) indicating a net loss of cells following treatment is calculated from [(Ti−Tz)/Tz]×100=−50. Values are calculated for each of these three parameters if the level of activity is reached; however, if the effect is not reached or is exceeded, the value for that parameter is expressed as greater or less than the maximum or minimum concentration tested.

The methods described were used to test compounds 70 and 71 on a panel of sixty cell lines under a screening service provided by the Developmental Therapeutics Program at the National Institutes of Health. Shown in FIG. 1C are 1, RPMI-8226 leukemia cells; 2; NCI-H322M non-small cell lung cancer cells; 3, HT29 colon cancer cells; 4, U251 CNS cancer cells; 5, SK-MEL-28 melanoma cancer cells; 6, SK-OV-3 ovarian cancer cells; 7, RXF 393 renal cancer cells; 8, PC-3 prostate cancer cells; 9, MDA-MB-231 breast cancer cells.

Results of testing compounds 70 and 71 against the full 60 cell lines are shown in the tables below. The testing was done by the National Cancer Institute Developmental Therapeutics Program. The results shown are in vitro testing results.

EXAMPLE 17

Figure 3:
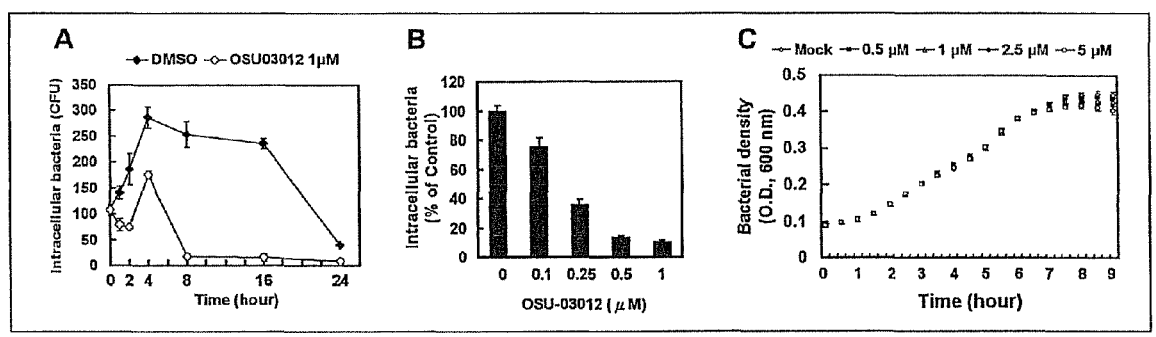

OSU-03012 eliminates intracellular *Salmonella typhimurium* from infected macrophages. The discovery that OSU-03012 induces autophagy in human cancer cells, coupled with the importance of autophagy as a defense against intracellular pathogens, prompted us to test the effect of this agent on the intracellular survival of *S. typhimurium* in infected RAW 264.7 murine macrophages. Both time- and dose-dependent effects of OSU-03012 were assessed in intracellular survival (i.e. gentamicin protection) assays. After 8 h of treatment, OSU-03012 caused dramatic reductions in intracellular bacterial survival with an $IC_{50}$ of ~0.2 µM and maximal inhibition at 1 µM (FIG. 3A, B). To determine if OSU-03012 had direct bactericidal activity, the effect of OSU-03012 on extracellular bacterial growth was examined in liquid medium (FIG. 3C) and on agar by the disc-diffusion method (not shown). In both systems, the growth of *S. typhimurium* was unaffected by OSU-03012 at concentrations of up to 5 µM. These findings indicate that OSU-03012 potently eliminates intracellular bacteria from phagocytes and that this activity is mediated via an indirect mechanism, presumably through effects on the host cell.

OSU-03012 eliminates intracellular *S. typhimurium* by inducing autophagy in infected macrophages. To demonstrate that the elimination of intracellular bacteria by OSU-03012 treatment is mediated by the induction of autophagy, infected RAW 264.7 cells were treated with 1 µM OSU-03012 for 8 h in the presence or absence of 3-methyladenine (3MA), a classical inhibitor of autophagy. FIG. 4A shows that 3MA completely blocked the ability of OSU-03012 reduce intracellular bacterial survival, strongly indicating that autophagy is essential to OSU-03012's ability to eliminate intracellular bacteria. Additional evidence for this mechanism of action comes from the human breast cancer cell lines, MCF-7 and MDA-MB-231, which differ in their expression levels of beclin-1, a tumor suppressor that is critical for the execution of autophagy (FIG. 5A). Accordingly, the ability of OSU-03012 to induce autophagy in these cell lines, as determined by the intensity of immunostaining for endogenous LC3, a marker of mammalian autophagosomes (FIG. 5C), correlates with their respective beclin-1 expression levels. Moreover, intracellular bacterial survival in OSU-03012-treated *S. typhimurium*-infected breast cancer cells also reflects their respective beclin-1 status (FIG. 5B). Rapamycin, an established inducer of autophagy, is also capable of suppressing survival of *S. typhimurium* in murine macrophages (FIG. 4B). However, in comparison to OSU-03012, a nearly 100-fold higher concentration of rapamycin is required to match the degree of bacterial clearance caused by OSU-03012. Taken together, these data strongly support that OSU-03012 eliminates intracellular pathogens by inducing autophagy in the host cell. Moreover, OSU-03012 induces autophagy and bacterial clearance far more potently than rapamycin and at clinically attainable concentrations.

OSU-03012 eliminates *F. novicida* from infected macrophages. To obtain data of direct relevance to the proposed studies, in collaboration with Dr. Schlesinger, RAW 264.7 cells were infected with *F. novicida* and treated with 1 µM OSU-03012 for 24 h. As shown in FIG. 6, OSU-03012 drastically reduced intracellular survival of *F. novicida*.

To demonstrate that OSU-03012 promotes bacterial clearance in *Francisella*-infected macrophages via the induction of autophagy. Rationale. The goal of this is to produce evidence indicating that OSU-03012, a novel small molecule inducer of autophagy, exhibits clinical potential as a therapeutic agent against *F. tularensis* infection. Using *F. novicida* initially and then moving to the virulent Type A strain of *F. tularensis* (Schu 4), and human macrophages as the host cell type, this will extend our studies in *S. typhimurium*-infected murine macrophages to a model of human infection. The proposed experiments are designed to assess the ability of OSU-03012 to inhibit intramacrophage survival of *F. tularensis* and to define a role for OSU-03012-induced host cell autophagy in mediating this effect.

Experimental Plan and Methods. Synthesis of OSU-03012. OSU-03012 has been synthesized in large quantities, as depicted in the following scheme, for in vivo testing in various tumor xenograft models of human cancer and in transgenic animals. OSU-03012 is orally bioavailable with favorable pharmacokinetic properties, and is currently undergoing preclinical evaluations under the RAID program at NCI.

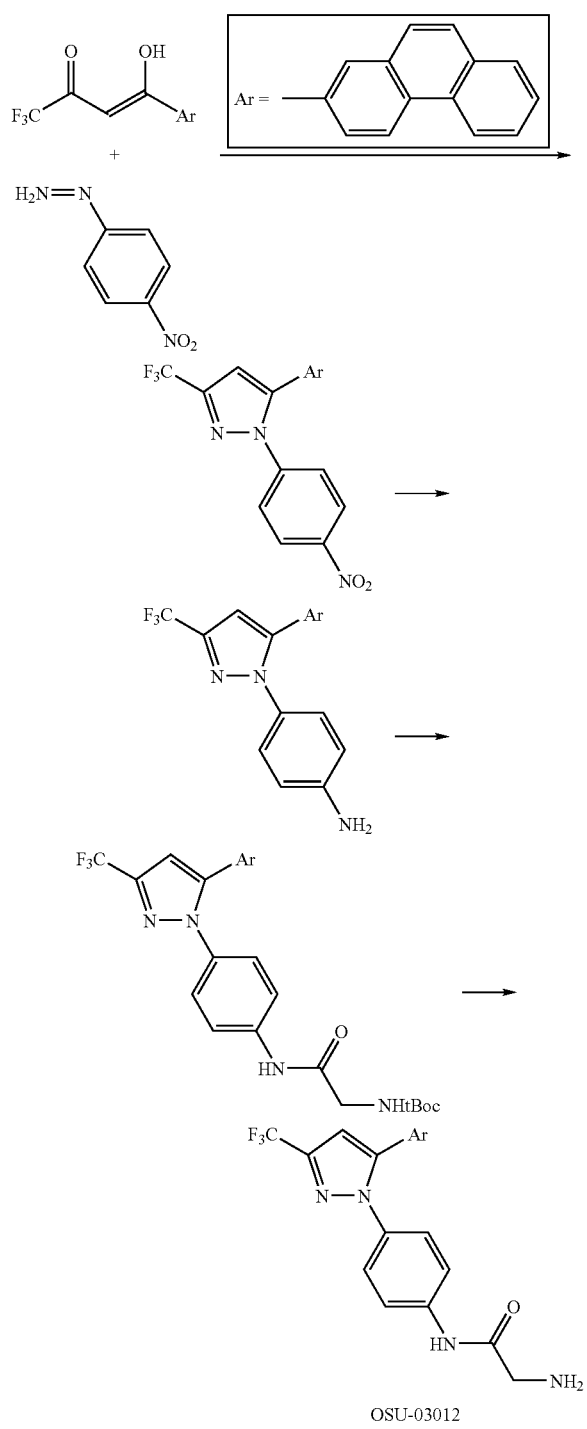

OSU-03012

Intracellular survival assay to assess *Francisella* survival in OSU-03012-treated macrophages. Monolayers of J774.1 murine macrophages, THP-1 human macrophages, and human monocyte-derived macrophages (MDM) will be infected with *Francisella* (MOI of 60:1). After 2 h incubation, extracellular bacteria will be eliminated by addition of gentamicin (50 μg/ml; 1 h), followed by washing and treatment with OSU-03012 at various concentrations (0.1-5 μM) and for different durations in the presence or absence of gentamicin (10 μg/ml). After treatments, macrophages will be lysed and the lysates serially diluted and plated on cysteine-supplemented Tryptic Soy Agar (TSA) for subsequent enumeration of CFU.

Evaluation of direct bactericidal effects of OSU-03012 on *Francisella*. To confirm that inhibition of *Francisella* intracellular survival by OSU-03012 is not a result of direct bactericidal activity against this pathogen, a bacterial growth assay will be performed. Late lag phase *Francisella* will be diluted into antibiotic-free, cysteine-supplemented Tryptic Soy Broth and treated with a range of OSU-03012 concentrations that encompasses those shown to suppress intracellular survival. Bacterial growth will be monitored by measurements of OD (600 nm) of the bacterial suspensions every 30 min until lag phase is reached.

Evaluation of cytotoxic effects of OSU-03012 on macrophages. The effect of OSU-03012 on the viability of uninfected J774.1 cells, THP-1 cells and MDMs will be evaluated with the 3-(4,5-dimethylthiazol-2-yl)-2,5-diphenyltetrazolium bromide (MTT) assay in a 96-well format. Macrophages will be treated with a range of OSU-03012 concentrations that encompasses those shown to effectively suppress intracellular survival. At the end of treatments, the reduced MTT dye will be solubilized and absorbances determined at 570 nm.

Autophagy assays. Pharmacological, immunocytochemical and siRNA approaches will be used to confirm the induction of autophagy by OSU-03012 in murine and human macrophages, and its role in bacterial killing.

Effect of autophagy inhibition on OSU-03012-induced suppression of bacterial survival. Intracellular survival assays will be performed to determine whether the classical inhibitor of autophagy, 3-methyladenine (3MA), can suppress the ability of OSU-03012 to induce bacterial clearance in macrophages. Likewise, siRNA-mediated knock-down of beclin-1, a tumor suppressor critical for the execution of autophagy, will be tested for a similar effect on OSU-03012-induced bacterial killing. The rescue of *Francisella* survival in OSU-03012-treated macrophages by autophagy inhibition would strongly suggest that an autophagic mechanism mediates OSU-03012 activity. These findings will be supported by the use of cells expressing GFP-labeled LC3, a specific marker of mammalian autophagosomal membranes. The proportion of cells exhibiting punctate distribution of GFP-LC3, indicative of autophagy, will be determined in infected macrophages treated with OSU-03012 in the presence and absence of 3MA- or beclin-1 siRNA-mediated inhibition of autophagy.

Autolysosome formation in OSU-03012-treated, *Francisella*-infected macrophages. Autophagosome-lysosome fusion and subsequent luminal acidification and lysosomal hydrolysis results in degradation of autophagocytosed entities. To determine if OSU-03012 induces autophagic maturation to autolysosome formation, *Francisella*-infected macrophages expressing GFP-LC3 will be treated with OSU-03012 at concentrations that effectively suppress bacterial survival, and then processed for immunofluorescence microscopy for the detection of the lysosomal marker, LAMP-1. Enhanced co-localization of GFP-LC3 and LAMP-1-immunopositivity in drug-treated cells would indicate autolysosome formation. Further evidence for this phenomenon will be examined in OSU-03012-treated macrophages infected with GFP-expressing *F. novicida*, or Schu 4 strain labeled with anti-Francisella Ab in which the acidotropic dye LysoTracker Red (LT) will be used to detect acidified bacteria-containing vacuoles. Increases in the proportion of drug-treated cells with LT-positive, bacteria-containing vacuoles would indicate stimulation of autolysosome formation.

TABLE 5

Results of testing Compound 70 against 60 cancer cell lines.

| Panel/Cell Line | Time Zero | Ctrl | Mean Optical Densities | | | | | Percent Growth | | | | | GI50 | TGI | LC50 |
|---|---|---|---|---|---|---|---|---|---|---|---|---|---|---|---|
| | | | -8.0 | -7.0 | -6.0 | -5.0 | -4.0 | -8.0 | -7.0 | -6.0 | -5.0 | -4.0 | | | |
| Leukemia | | | | | | | | | | | | | | | |
| CCRF-CEM | 0.295 | 1.099 | 0.893 | 0.946 | 0.523 | 0.168 | 0.194 | 74 | 81 | 28 | -43 | -34 | 3.87E-07 | 2.49E-06 | >1.00E-04 |
| K-562 | 0.297 | 1.467 | 1.435 | 1.022 | 0.681 | 0.209 | 0.247 | 97 | 62 | 33 | -30 | -17 | 2.57E-07 | 3.34E-06 | >1.00E-04 |
| MOLT-4 | 0.313 | 1.048 | 0.964 | 0.951 | 0.614 | 0.180 | 0.296 | 89 | 87 | 41 | -42 | -6 | 6.36E-07 | 3.10E-06 | >1.00E-04 |
| RPMI-B226 | 0.332 | 0.845 | 0.756 | 0.701 | 0.547 | 0.164 | 0.229 | 85 | 72 | 42 | -51 | -31 | 5.37E-07 | 2.84E-06 | — |
| SR | 0.364 | 0.902 | 0.816 | 0.796 | 0.605 | 0.265 | 0.363 | 84 | 80 | 45 | -27 | — | 7.11E-07 | 4.17E-06 | >1.00E-04 |
| Non-Small Cell Lung Cancer | | | | | | | | | | | | | | | |
| A549/ATCC | 0.363 | 1.279 | 1.294 | 1.149 | 0.831 | 0.155 | 0.252 | 102 | 86 | 51 | -57 | -31 | 1.02E-06 | 2.96E-06 | — |
| EKVX | 0.557 | 0.860 | 0.891 | 0.860 | 0.786 | 0.156 | 0.193 | 110 | 100 | 75 | -72 | -65 | 1.49E-06 | 3.25E-06 | 7.08E-06 |
| HOP-62 | 0.510 | 1.395 | 1.310 | 1.330 | 1.075 | 0.155 | 0.217 | 90 | 93 | 64 | -70 | -57 | 1.27E-06 | 3.01E-06 | 7.13E-06 |
| HOP-92 | 1.070 | 1.526 | 1.509 | 1.474 | 1.465 | 0.095 | 0.267 | 96 | 89 | 87 | -91 | -75 | 1.61E-06 | 3.07E-06 | 5.87E-06 |
| NCI-H226 | 1.190 | 1.594 | 1.593 | 1.586 | 1.429 | 0.505 | 0.614 | 100 | 98 | 59 | -58 | -48 | 1.20E-06 | 3.21E-06 | — |
| NCI-H23 | 0.457 | 1.655 | 1.672 | 1.673 | 1.255 | 0.097 | 0.156 | 101 | 102 | 67 | -79 | -66 | 1.30E-06 | 2.87E-06 | 6.33E-06 |
| NCI-H322M | 0.626 | 2.465 | 1.363 | 1.562 | 1.420 | 0.100 | 0.269 | 40 | 51 | 43 | -84 | -57 | — | 2.18E-06 | 5.40E-06 |
| NCI-H46D | 0.319 | 1.843 | 1.799 | 1.499 | 0.830 | 0.173 | 0.213 | 97 | 77 | 34 | -46 | -33 | 4.21E-07 | 2.64E-06 | >1.00E-04 |
| NCI-H522 | 0.766 | 1.549 | 1.626 | 1.718 | 1.528 | 0.260 | 0.486 | 110 | 122 | 97 | -66 | -37 | 1.95E-06 | 3.94E-06 | — |
| Colon Cancer | | | | | | | | | | | | | | | |
| COLO 205 | 0.221 | 1.412 | 1.286 | 1.252 | 0.916 | 0.104 | 0.239 | 89 | 87 | 58 | -53 | 1 | 1.19E-06 | — | — |
| HCT-116 | 0.114 | 0.708 | 0.751 | 0.665 | 0.452 | 0.104 | 0.146 | 107 | 93 | 57 | -9 | 5 | 1.27E-06 | — | >1.00E-04 |
| HCT-15 | 0.279 | 0.875 | 0.760 | 0.599 | 0.561 | 0.149 | 0.278 | 81 | 54 | 47 | -47 | — | 3.65E-07 | 3.19E-06 | >1.00E-04 |
| HT29 | 0.215 | 1.453 | 1.355 | 1.299 | 0.801 | 0.075 | 0.159 | 92 | 88 | 47 | -65 | -26 | 8.58E-07 | 2.64E-06 | — |
| KM12 | 0.535 | 2.184 | 2.151 | 2.044 | 1.425 | 0.146 | 0.264 | 98 | 91 | 54 | -73 | -51 | 1.07E-06 | 2.67E-06 | 6.62E-06 |
| SW-620 | 0.187 | 1.202 | 1.197 | 1.198 | 0.736 | 0.127 | 0.136 | 100 | 100 | 54 | -32 | -28 | 1.12E-06 | 4.23E-06 | >1.00E-04 |
| CNS Cancer | | | | | | | | | | | | | | | |
| SF-268 | 0.376 | 1.142 | 1.016 | 0.930 | 0.789 | 0.252 | 0.280 | 84 | 72 | 54 | -33 | -26 | 1.11E-06 | 4.16E-06 | >1.00E-04 |
| SF-295 | 0.421 | 1.224 | 1.173 | 1.190 | 0.915 | 0.225 | 0.287 | 94 | 96 | 62 | -47 | -32 | 1.28E-06 | 3.71E-06 | >1.00E-04 |
| SNB-19 | 0.532 | 1.721 | 1.562 | 1.655 | 1.230 | 0.219 | 0.324 | 87 | 94 | 59 | -59 | -39 | 1.18E-06 | 3.15E-06 | — |
| U251 | 0.391 | 1.301 | 1.298 | 1.139 | 0.810 | 0.144 | 0.320 | 100 | 82 | 46 | -63 | -18 | 7.75E-07 | 2.64E-06 | — |
| Melanoma | | | | | | | | | | | | | | | |
| LOX IMVI | 0.353 | 1.166 | 1.204 | 0.974 | 0.742 | 0.176 | 0.352 | 105 | 76 | 48 | -50 | — | 8.36E-07 | 3.07E-06 | — |
| MALME-3M | 0.666 | 1.165 | 1.123 | 1.128 | 1.102 | 0.218 | 0.290 | 92 | 93 | 87 | -67 | -56 | 1.74E-06 | 3.67E-06 | 7.73E-06 |
| M14 | 0.315 | 0.986 | 0.975 | 0.974 | 0.916 | 0.211 | 0.256 | 98 | 98 | 90 | -33 | -19 | 2.10E-06 | 5.37E-06 | >1.00E-04 |
| SK-MEL-2 | 0.456 | 0.883 | 0.943 | 0.956 | 0.885 | 0.289 | 0.330 | 114 | 117 | 100 | -37 | -28 | 2.33E-06 | 5.40E-06 | >1.00E-04 |
| SK-MEL-28 | 0.530 | 1.482 | 1.426 | 1.320 | 1.130 | 0.071 | 0.218 | 94 | 83 | 63 | -87 | -59 | 1.22E-06 | 2.64E-06 | 5.69E-06 |
| SK-MEL-5 | 0.549 | 2.147 | 1.995 | 1.958 | 1.659 | 0.136 | 0.364 | 91 | 88 | 69 | -75 | -34 | 1.36E-06 | 3.02E-06 | — |
| UACC-62 | 0.675 | 1.600 | 1.649 | 1.546 | 1.407 | 0.137 | 0.364 | 105 | 94 | 79 | -80 | -46 | 1.53E-06 | 3.15E-06 | — |
| Ovarian Cancer | | | | | | | | | | | | | | | |
| IGROV1 | 0.462 | 1.060 | 1.044 | 1.103 | 0.902 | 0.235 | 0.302 | 97 | 107 | 74 | -49 | -35 | 1.56E-06 | 3.97E-06 | >1.00E-04 |
| OVCAR-3 | 0.460 | 0.929 | 0.879 | 0.849 | 0.816 | 0.140 | 0.301 | 89 | 83 | 76 | -70 | -35 | 1.51E-06 | 3.32E-06 | — |
| OVCAR-4 | 0.530 | 1.121 | 1.114 | 1.073 | 1.086 | 0.093 | 0.172 | 99 | 92 | 94 | -82 | -68 | 1.78E-06 | 3.41E-06 | 6.55E-06 |
| OVCAR-5 | 0.512 | 1.507 | 1.480 | 1.540 | 1.412 | 0.087 | 0.149 | 97 | 103 | 90 | -83 | -71 | 1.71E-06 | 3.32E-06 | 6.45E-06 |
| OVCAR-8 | 0.400 | 1.101 | 1.078 | 1.114 | 0.755 | 0.269 | 0.306 | 97 | 102 | 51 | -33 | -24 | 1.02E-06 | 4.05E-06 | >1.00E-04 |
| SK-OV-3 | 0.399 | 1.623 | 1.514 | 1.597 | 1.262 | 0.083 | 0.302 | 91 | 98 | 71 | -79 | -24 | 1.37E-06 | 2.96E-06 | — |
| Renal cancer | | | | | | | | | | | | | | | |
| 78G-0 | 0.652 | 1.958 | 2.012 | 1.897 | 1.440 | 0.181 | 0.299 | 104 | 95 | 60 | -72 | -54 | 1.20E-06 | 2.85E-06 | 6.79E-06 |
| A498 | 0.945 | 2.261 | 2.230 | 2.598 | 2.201 | 0.660 | 0.433 | 98 | 126 | 95 | -30 | -54 | 2.30E-06 | 5.75E-06 | 6.69E-05 |
| ACHN | 0.374 | 1.026 | 0.985 | 1.037 | 0.829 | 0.150 | 0.313 | 94 | 102 | 70 | -60 | -16 | 1.42E-06 | 3.45E-06 | — |
| CAKI-1 | 0.597 | 1.862 | 1.692 | 1.802 | 1.126 | 0.147 | 0.335 | 87 | 95 | 42 | -75 | -44 | 7.03E-07 | 2.27E-06 | — |
| RXP 393 | 0.403 | 0.801 | 0.766 | 0.700 | 0.628 | 0.177 | 0.441 | 91 | 75 | 56 | -56 | 10 | 1.14E-06 | — | — |
| SN12C | 0.584 | 1.233 | 1.209 | 1.194 | 1.093 | 0.203 | 0.308 | 96 | 94 | 78 | -65 | -47 | 1.58E-06 | 3.51E-06 | — |
| TK-10 | 0.672 | 1.496 | 1.512 | 1.492 | 1.304 | 0.138 | 0.200 | 102 | 100 | 77 | -80 | -70 | 1.48E-06 | 3.10E-06 | 6.47E-06 |
| UO-31 | 0.443 | 1.782 | 1.572 | 1.563 | 1.356 | 0.161 | 0.285 | 84 | 84 | 68 | -64 | -36 | 1.37E-06 | 3.29E-06 | — |
| Prostate Cancer | | | | | | | | | | | | | | | |
| PC-3 | 0.242 | 0.996 | 0.910 | 0.763 | 0.593 | 0.055 | 0.108 | 89 | 69 | 47 | -77 | -55 | 7.05E-07 | 2.38E-06 | 6.02E-06 |
| DU-145 | 0.327 | 0.961 | 0.993 | 1.018 | 0.895 | 0.078 | 0.132 | 105 | 109 | 90 | -76 | -60 | 1.73E-06 | 3.47E-06 | 6.95E-06 |
| Breast cancer | | | | | | | | | | | | | | | |
| MCF7 | 0.452 | 1.672 | 1.566 | 1.541 | 0.982 | 0.196 | 0.255 | 91 | 89 | 43 | -57 | -44 | 7.18E-07 | 2.72E-06 | — |
| NCI/ADR-RES | 0.556 | 1.904 | 1.883 | 1.878 | 1.217 | 0.229 | 0.212 | 98 | 98 | 49 | -59 | -62 | 9.54E-07 | 2.85E-06 | 8.28E-06 |
| MDA-MB-231/ATCC | 0.642 | 0.988 | 0.908 | 0.889 | 0.843 | 0.173 | 0.306 | 100 | 71 | 58 | -73 | -52 | 1.15E-06 | 2.77E-06 | 6.67E-06 |
| HS 57BT | 0.534 | 1.186 | 1.221 | 1.179 | 1.110 | 0.351 | 0.333 | 105 | 99 | 88 | -34 | -38 | 2.05E-06 | 5.25E-06 | >1.00E-04 |
| MDA-MB-435 | 0.404 | 1.469 | 1.502 | 1.447 | 1.126 | 0.127 | 0.347 | 103 | 98 | 68 | -69 | -14 | 1.35E-06 | 3.14E-06 | — |

TABLE 5-continued

Results of testing Compound 70 against 60 cancer cell lines.

|  |  | \multicolumn{11}{c}{Log10 concentration} |  |  |  |
|---|---|---|---|---|---|---|---|---|---|---|---|---|---|---|
| Panel/Cell | Time | \multicolumn{5}{c}{Mean Optical Densities} | \multicolumn{5}{c}{Percent Growth} |  |  |  |
| Line | Zero | Ctrl | −8.0 | −7.0 | −6.0 | −5.0 | −4.0 | −8.0 | −7.0 | −6.0 | −5.0 | −4.0 | GI50 | TGI | LC50 |
|---|---|---|---|---|---|---|---|---|---|---|---|---|---|---|---|
| BT-549 | 0.492 | 0.957 | 0.912 | 0.891 | 0.785 | 0.143 | 0.195 | 90 | 86 | 63 | −71 | −60 | 1.25E−06 | 2.95E−06 | 6.98E−06 |
| T-47D | 0.423 | 1.019 | 0.921 | 1.071 | 0.935 | 0.205 | 0.238 | 84 | 109 | 86 | −52 | −44 | 1.82E−06 | 4.21E−06 | — |

TABLE 6

Results of testing Compound 71 against 60 cancer cell lines.

|  |  | \multicolumn{11}{c}{Log10 Concentration} |  |  |  |
|---|---|---|---|---|---|---|---|---|---|---|---|---|---|---|
| Panel/Cell | Time | \multicolumn{5}{c}{Mean Optical Densities} | \multicolumn{5}{c}{Percent Growth} |  |  |  |
| Line | Zero | Ctrl | −8.0 | −7.0 | −6.0 | −5.0 | −4.0 | −8.0 | −7.0 | −6.0 | −5.0 | −4.0 | GI50 | TGI | LC50 |
|---|---|---|---|---|---|---|---|---|---|---|---|---|---|---|---|
| \multicolumn{16}{c}{Leukemia} |
| CCRF-CEM | 0.295 | 0.949 | 0.808 | 0.811 | 0.718 | 0.002 | 0.140 | 78 | 79 | 65 | −99 | −53 | 1.23E−06 | 2.48E−06 | 5.00E−06 |
| K-562 | 0.297 | 1.401 | 1.338 | 1.283 | 0.438 | 0.126 | 0.119 | 94 | 89 | 13 | −58 | −60 | 3.26E−07 | 1.52E−06 | 7.77E−06 |
| MOLT-4 | 0.313 | 0.957 | 0.833 | 0.736 | 0.461 | 0.143 | 0.143 | 81 | 66 | 23 | −54 | −54 | 2.33E−07 | 1.98E−06 | 8.75E−06 |
| RPMI-8226 | 0.332 | 0.682 | 0.536 | 0.559 | 0.513 | 0.016 | 0.176 | 58 | 65 | 52 | −95 | −47 | 1.03E−06 | 2.25E−06 | — |
| SR | 0.364 | 0.888 | 0.688 | 0.583 | 0.254 | 0.234 | 0.287 | 62 | 42 | −30 | −36 | −21 | 3.86E−08 | 3.79E−07 | >1.00E−04 |
| \multicolumn{16}{c}{Non-Small Cell Lung Cancer} |
| A549/ATCC | 0.363 | 1.175 | 1.140 | 1.145 | 1.121 | −0.032 | 0.135 | 96 | 96 | 93 | −100 | −63 | 1.68E−06 | 3.04E−06 | 5.51E−06 |
| EKVX | 0.557 | 0.841 | 0.713 | 0.737 | 0.711 | −0.008 | 0.145 | 55 | 63 | 54 | −100 | −74 | 1.06E−06 | 2.24E−06 | 4.74E−06 |
| HOP-62 | 0.510 | 1.288 | 1.285 | 1.267 | 1.255 | 0.011 | 0.329 | 100 | 97 | 96 | −98 | −36 | 1.72E−06 | 3.12E−06 | — |
| HOP-92 | 1.070 | 1.647 | 1.567 | 1.541 | 1.361 | 0.089 | 0.767 | 86 | 82 | 50 | −92 | −28 | 1.01E−06 | 2.26E−06 | — |
| NCI-H23 | 0.457 | 1.669 | 1.585 | 1.515 | 1.679 | −0.041 | 0.151 | 93 | 87 | 101 | −100 | −67 | 1.79E−06 | 3.18E−06 | 5.64E−06 |
| NCI-H322H | 0.626 | 1.181 | 0.988 | 1.049 | 1.031 | −0.052 | 0.257 | 65 | 76 | 73 | −100 | −59 | 1.36E−06 | 2.64E−06 | 5.14E−06 |
| NCI-H460 | 0.319 | 1.792 | 1.654 | 1.658 | 1.650 | 0.011 | 0.257 | 91 | 91 | 90 | −97 | −20 | 1.64E−06 | 3.04E−06 | — |
| NCI-H522 | 0.766 | 1.671 | 1.509 | 1.558 | 1.471 | 0.037 | 0.439 | 82 | 87 | 78 | −95 | −43 | 1.45E−06 | 2.82E−06 | — |
| \multicolumn{16}{c}{Colon Cancer} |
| COLO 205 | 0.221 | 1.196 | 1.146 | 1.028 | 0.930 | 0.009 | 0.151 | 95 | 83 | 73 | −96 | −32 | 1.36E−06 | 2.69E−06 | — |
| HCT-116 | 0.114 | 0.714 | 0.607 | 0.633 | 0.525 | −0.022 | 0.058 | 82 | 86 | 68 | −100 | −49 | 1.29E−06 | 2.55E−06 | — |
| HCT-15 | 0.279 | 0.893 | 0.669 | 0.779 | 0.797 | −0.003 | 0.082 | 64 | 81 | 84 | −100 | −71 | 1.54E−06 | 2.87E−06 | 5.36E−06 |
| HT29 | 0.215 | 1.333 | 1.276 | 1.238 | 1.136 | −0.054 | 0.003 | 95 | 91 | 82 | −100 | −99 | 1.50E−06 | 2.83E−06 | 5.32E−06 |
| KM12 | 0.535 | 1.957 | 1.867 | 1.832 | 1.777 | 0.013 | 0.307 | 94 | 91 | 87 | −98 | −43 | 1.59E−06 | 2.97E−06 | — |
| SW-620 | 0.187 | 1.073 | 0.923 | 0.993 | 1.060 | −0.048 | 0.015 | 83 | 91 | 98 | −100 | −92 | 1.75E−06 | 3.13E−06 | 5.60E−06 |
| \multicolumn{16}{c}{CNS Cancer} |
| SF-268 | 0.376 | 1.016 | 0.893 | 0.939 | 0.886 | 0.148 | 0.278 | 81 | 88 | 80 | −61 | −26 | 1.63E−06 | 3.69E−06 | — |
| SF-295 | 0.421 | 1.107 | 1.033 | 0.931 | 0.997 | −0.025 | 0.195 | 89 | 74 | 84 | −100 | −54 | 1.53E−06 | 2.86E−06 | 5.35E−06 |
| SNB-19 | 0.532 | 1.483 | 1.385 | 1.385 | 1.351 | 0.063 | 0.317 | 90 | 90 | 86 | −88 | −40 | 1.61E−06 | 3.12E−06 | — |
| U251 | 0.391 | 1.156 | 1.125 | 1.059 | 1.123 | 0.026 | 0.484 | 96 | 87 | 96 | −93 | 12 | 1.74E−06 | — | — |
| \multicolumn{16}{c}{Melanoma} |
| LOX IMVI | 0.353 | 1.164 | 0.948 | 1.033 | 0.935 | 0.008 | 0.165 | 73 | 84 | 72 | −98 | −53 | 1.34E−06 | 2.65E−06 | 5.22E−06 |
| MALME-3M | 0.666 | 0.984 | 0.832 | 0.838 | 0.826 | 0.089 | 0.333 | 52 | 54 | 50 | −87 | −50 | 1.01E−06 | 2.33E−06 | 1.00E−04 |
| M14 | 0.315 | 0.935 | 0.772 | 0.823 | 0.816 | −0.004 | 0.210 | 74 | 82 | 81 | −100 | −33 | 1.48E−06 | 2.80E−06 | — |
| SK-MEL-1 | 0.456 | 0.830 | 0.775 | 0.819 | 0.780 | −0.010 | 0.324 | 85 | 97 | 87 | −100 | −29 | 1.57E−06 | 2.91E−06 | — |
| SK-MEL-28 | 0.530 | 1.508 | 1.439 | 1.408 | 1.367 | −0.002 | 0.248 | 93 | 90 | 86 | −100 | −53 | 1.56E−06 | 2.89E−06 | 5.38E−06 |
| SK-MEL-5 | 0.549 | 1.640 | 1.611 | 1.762 | 1.812 | 0.143 | 0.363 | 97 | 111 | 116 | −74 | −34 | 2.22E−06 | 4.07E−06 | — |
| UACC-62 | 0.675 | 1.477 | 1.323 | 1.338 | 1.301 | −0.041 | 0.272 | 81 | 83 | 78 | −100 | −60 | 1.44E−06 | 2.74E−06 | 5.24E−06 |
| \multicolumn{16}{c}{Ovarian Cancer} |
| IGROV1 | 0.462 | 1.091 | 0.997 | 0.983 | 0.806 | −0.039 | 0.216 | 85 | 83 | 55 | −100 | −53 | 1.07E−06 | 2.26E−06 | 4.75E−06 |
| OVCAR-3 | 0.460 | 0.868 | 0.833 | 0.792 | 0.770 | −0.043 | 0.131 | 91 | 81 | 76 | −100 | −72 | 1.40E−06 | 2.70E−06 | 5.20E−06 |
| OVCAR-4 | 0.530 | 1.123 | 1.011 | 0.999 | 0.945 | −0.001 | 0.179 | 81 | 79 | 70 | −100 | −66 | 1.31E−06 | 2.58E−06 | 5.08E−06 |
| OVCAR-5 | 0.512 | 1.592 | 1.538 | 1.437 | 1.559 | −0.033 | 0.474 | 95 | 86 | 97 | −100 | −8 | 1.73E−06 | 3.11E−06 | — |
| OVCAR-8 | 0.400 | 0.968 | 0.923 | 0.946 | 0.934 | −0.001 | 0.126 | 92 | 96 | 94 | −100 | −69 | 1.69E−06 | 3.05E−06 | 5.52E−06 |
| SK-OV-3 | 0.399 | 1.327 | 1.261 | 1.245 | 1.093 | 0.062 | 0.278 | 93 | 91 | 75 | −85 | −30 | 1.43E−06 | 2.94E−06 | — |
| \multicolumn{16}{c}{Renal Cancer} |
| 786-0 | 0.652 | 1.912 | 1.862 | 1.868 | 1.663 | 0.046 | 0.458 | 96 | 96 | 80 | −93 | −30 | 1.49E−06 | 2.91E−06 | — |
| A498 | 0.945 | 2.207 | 2.413 | 2.087 | 1.869 | 1.903 | 0.540 | 116 | 91 | 73 | 76 | −43 | 1.65E−05 | 4.35E−05 | >1.00E−04 |
| ACHN | 0.374 | 1.026 | 0.898 | 0.902 | 0.964 | 0.034 | 0.291 | 80 | 81 | 90 | −91 | −22 | 1.67E−06 | 3.15E−06 | — |
| CAKI-1 | 0.597 | 1.767 | 1.735 | 1.642 | 1.804 | −0.067 | 0.315 | 97 | 89 | 103 | −100 | −47 | 1.83E−06 | 3.22E−06 | — |
| RXF 393 | 0.403 | 0.829 | 0.582 | 0.629 | 0.629 | 0.156 | 0.385 | 42 | 53 | 53 | −61 | −4 | — | 2.91E−06 | — |
| SN12C | 0.584 | 1.115 | 1.050 | 0.998 | 1.045 | −0.014 | 0.224 | 88 | 78 | 87 | −100 | −62 | 1.57E−06 | 2.91E−06 | 5.40E−06 |

TABLE 6-continued

Results of testing Compound 71 against 60 cancer cell lines.

| Panel/Cell Line | Time Zero | Ctrl | Mean Optical Densities | | | | | Percent Growth | | | | | GI50 | TGI | LC50 |
|---|---|---|---|---|---|---|---|---|---|---|---|---|---|---|---|
| | | | −8.0 | −7.0 | −6.0 | −5.0 | −4.0 | −8.0 | −7.0 | −6.0 | −5.0 | −4.0 | | | |
| TK-10 | 0.672 | 1.134 | 1.032 | 1.087 | 0.998 | −0.021 | 0.245 | 78 | 90 | 71 | −100 | −64 | 1.32E−06 | 2.59E−06 | 5.09E−06 |
| UO-31 | 0.443 | 1.467 | 1.375 | 1.407 | 1.332 | −0.030 | 0.288 | 91 | 94 | 87 | −100 | −35 | 1.57E−06 | 2.92E−06 | — |
| Prostate Cancer | | | | | | | | | | | | | | | |
| PC-3 | 0.242 | 1.068 | 0.862 | 0.846 | 0.857 | −0.022 | 0.179 | 75 | 73 | 75 | −100 | −26 | 1.38E−06 | 2.67E−06 | — |
| DU-145 | 0.327 | 0.835 | 0.694 | 0.767 | 0.760 | −0.074 | −0.019 | 72 | 87 | 85 | −100 | −100 | 1.55E−06 | 2.89E−06 | 5.37E−06 |
| Breast Cancer | | | | | | | | | | | | | | | |
| MCF7 | 0.452 | 1.540 | 1.467 | 1.340 | 1.507 | 0.073 | 0.229 | 93 | 82 | 97 | −84 | −49 | 1.82E−06 | 3.44E−06 | — |
| NCI/ADR-RES | 0.556 | 1.942 | 1.920 | 1.882 | 1.874 | 0.490 | 0.294 | 98 | 96 | 95 | −12 | −47 | 2.64E−06 | 7.73E−06 | >1.00E−04 |
| MDA-MB-231/ATCC | 0.642 | 0.884 | 0.756 | 0.830 | 0.709 | 0.015 | 0.389 | 47 | 78 | 27 | −98 | −39 | — | 1.66E−06 | — |
| HS 578T | 0.534 | 1.167 | 1.099 | 1.165 | 1.127 | 0.168 | 0.333 | 89 | 100 | 94 | −69 | −38 | 1.86E−06 | 3.78E−06 | — |
| MDA-MB-435 | 0.404 | 1.498 | 1.376 | 1.382 | 1.444 | −0.073 | 0.295 | 89 | 89 | 95 | −100 | −27 | 1.70E−06 | 3.07E−06 | — |
| T-47D | 0.423 | 0.750 | 0.541 | 0.578 | 0.529 | 0.100 | 0.198 | 36 | 47 | 32 | −76 | −53 | <1.00E−08 | 1.98E−06 | 5.72E−06 |

The examples described herein are meant to be illustrative of the synthesis and applications of the compounds described. The examples are not meant to limit the scope of the invention described herein.

TABLE 7

Treatment groups & mouse numbers: Total = 250 mice

| | | Treatments | | | |
|---|---|---|---|---|---|
| | | Gentamicin[B] | OSU-03012 (mg/kg; p.o., QD)[A] | | |
| Regimen | Vehicle | (100 μg, i.n.) | 50 | 100 | 200 |
| A[C] | 20 | 20 | 20 | 20 | 20 |
| B[C] | 20 | 20 | 20 | 20 | 20 |
| C | 10 | 10 | 10 | 10 | 10 |

[A]These doses of OSU-03012 are based on our experience with this agent in mouse models of cancers in which these doses caused dose-dependent suppression of tumor growth, and attained average plasma levels of 8-10 μM. This plasma level is higher than that shown in our preliminary studies to induce bacterial clearance and autophagy in murine macrophages and human breast cancer cells.
[B]Experiments for each Regimen will be conducted separately; thus each requires its own gentamicin treatment group.
[C]Mouse numbers for each group in Regimens A and B include 10 mice to be sacrificed at 24 h post-infection for assessment of bacterial load in target organs.

The invention claimed is:

1. A compound of Formula I

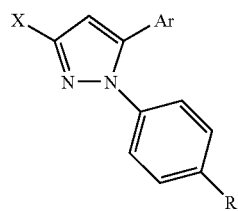

I wherein X is —CF$_3$, Ar is

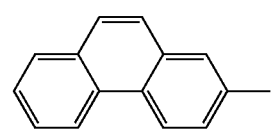

and R is selected from

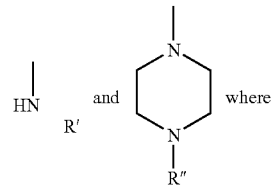

where

R' is is SO$_2$CH$_2$CH$_2$NH$_2$, or SO$_2$NH$_2$ or an amino acid attached through the α-carboxyl group selected from the group consisting of L-Lys, D-Lys, β-Ala, L-Lue, L-Ile, Phe, Asn, Glu and Gyl, and R" is methyl, ethyl, allyl, CH$_2$CH$_2$OH, CH$_2$CN, CH$_2$CH$_2$CN, CH$_2$CONH$_2$,

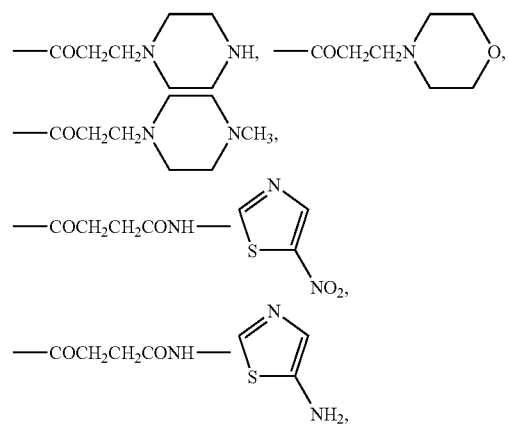

-continued

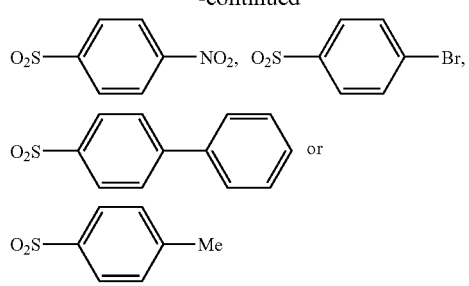

or pharmaceutically acceptable salts thereof.

2. The compound of claim 1 wherein the compound has the following Formula VI

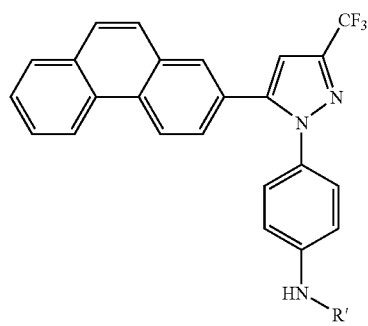

R' = L-Lys, MW: 531.57
    D-Lys, MW: 531.57
    β-Ala, MW: 474.48
    L-Lue
    L-Ile
    Phe
    SO2CH2CH2NH2, MW: 510.53
    SO2NH2, MW: 482.48 or pharmaceutically acceptable salts thereof.

3. The compound of claim 1 wherein the compound has the following Formula VII

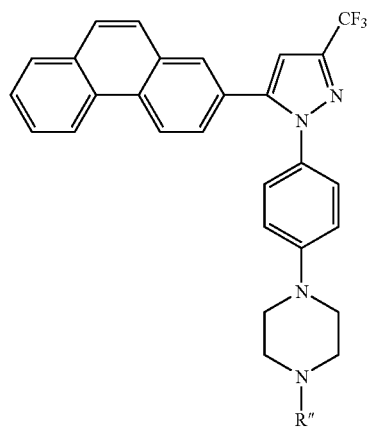

R'' = H, MW: 472.50
    Gly, MW: 529.56 or pharmaceutically acceptable salts thereof.

4. The compound of claim 1 wherein the compound has the following Formula XIV

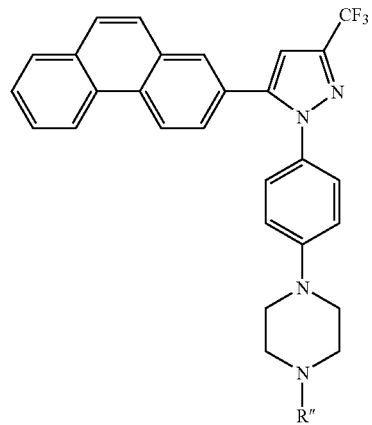

where

| | | |
|---|---|---|
| N4NBS | R'' = $O_2S$-C$_6$H$_4$-NO$_2$ | MW 657.66 |
| N4BPS | R'' = $O_2S$-C$_6$H$_4$-Br | MW 688.72 |
| N4BBS | R'' = $O_2S$-C$_6$H$_4$-C$_6$H$_5$ | MW 691.56 |
| N4MBS | R'' = $O_2S$-C$_6$H$_4$-Me | MW 626.69 |
| N4ME | R'' = Me | MW 486.53 |
| N4E | R'' = Et | MW 500.56 |
| N4ALL | R'' = Allyl | MW 512.57 |
| N4HE | R'' = CH2CH2OH | MW 516.56 |
| N4ACN | R'' = CH2CN | MW 511.54 |
| N4PCN | R'' = CH2CH2CN | MW 525.57 |
| N4ETFM | R'' = CH2CH2CF3 | MW 568.56 |
| N4AA | R'' = CH2CONH2 | | or pharmaceutically acceptable salts thereof.

5. A compound of the following Formula IX

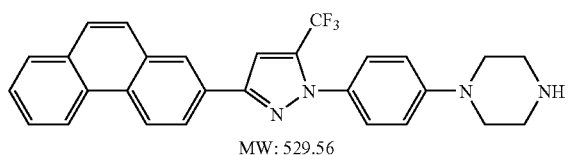

MW: 529.56 or pharmaceutically acceptable salts thereof.

6. A method of inducing apoptosis in cancer cells selected from the group consisting of leukemia, non-small cell lung cancer, colon cancer, central nervous system cancer, melanoma, ovarian cancer, renal cancer, prostate cancer, and breast cancer cells, the method comprising the step of contacting a therapeutically effective amount of a compound of Formula I

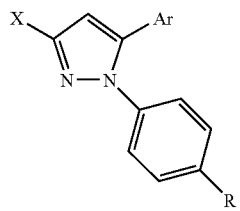

wherein X is —CF$_3$, Ar is

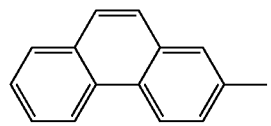

and R is selected from

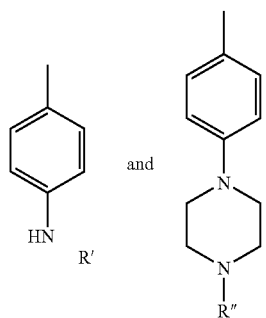

where

R' is is SO$_2$CH$_2$CH$_2$NH$_2$, or SO$_2$NH$_2$ or an amino acid attached through the α-carboxyl group selected from the group consisting of L-Lys, D-Lys, β-Ala, L-Lue, L-Ile, Phe, Asn, Glu and Gyl, and R" is methyl, ethyl, allyl, CH$_2$CH$_2$OH, CH$_2$CN, CH$_2$CH$_2$CN, CH$_2$CONH$_2$,

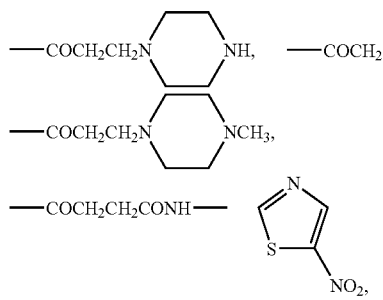

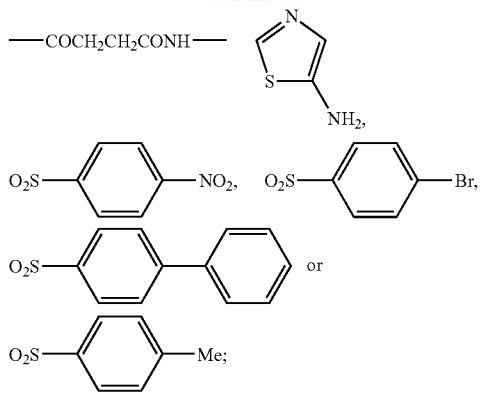

or pharmaceutically acceptable salts thereof, with the rapidly proliferating cells.

7. A method for treating, inhibiting, or delaying the onset of cancer, wherein the cancer is selected from the group consisting of leukemia, non-small cell lung cancer, colon cancer, central nervous system cancer, melanoma, ovarian cancer, renal cancer, prostate cancer, and breast cancer, in a subject in need of such treatment, the method comprising administering a therapeutically effective amount of a compound of Formula I:

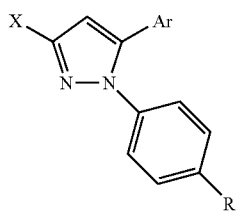

wherein X is —CF$_3$, Ar is

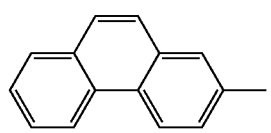

and R is selected from

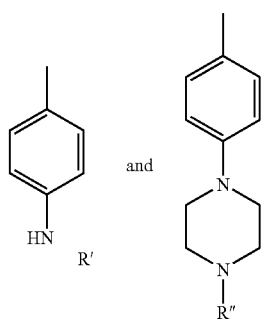

where

R' is is $SO_2CH_2CH_2NH_2$, or $SO_2NH_2$ or an amino acid attached through the α-carboxyl group selected from the group consisting of L-Lys, D-Lys, β-Ala, L-Lue, L-Ile, Phe, Asn, Glu and Gyl, and R" is methyl, ethyl, allyl, $CH_2CH_2OH$, $CH_2CN$, $CH_2CH_2CN$, $CH_2CONH_2$,

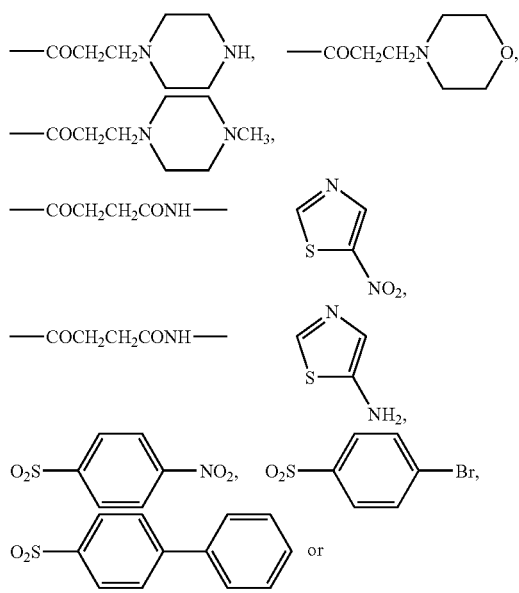

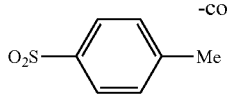

or pharmaceutically acceptable salts thereof, to the subject in need of such treatment.

8. The method of claim 7 wherein the subject is a human.

9. A method of inducing autophagy in cells infected by an intracellular bacteria comprising administering to a subject diagnosed with a disease caused by the bacteria a therapeutically effective amount of at least one compound selected from Formula I, VI, VII, IX, and XIV.

10. The method according to claim 9, wherein the subject is an animal.

11. The method according to claim 10, wherein the subject is a human.

12. The method according to claim 9, wherein the bacteria is chosen from *Mycobacterium tuberculosis, Francisella tularensis, Streptococcus pyogenes, Rickettsiae* spp., and *Salmonella typhimurium.*

13. A method of reducing the release of bacterial endotoxins in a subject comprising administering to a subject that has undergone antibiotic treatment a therapeutically effective amount of at least one compound selected from Formula I, VI, VII, IX, and XIV.

14. The method according to claim 13, wherein the subject is an animal.

15. The method according to claim 14, wherein the subject is a human.

\* \* \* \* \*

UNITED STATES PATENT AND TRADEMARK OFFICE
CERTIFICATE OF CORRECTION

PATENT NO. : 8,039,502 B2
APPLICATION NO. : 12/179134
DATED : October 18, 2011
INVENTOR(S) : Ching-Shih Chen et al.

Page 1 of 1

It is certified that error appears in the above-identified patent and that said Letters Patent is hereby corrected as shown below:

In the Specification

Column 1, Lines 17-20 replace the Government Support Clause with:
--This invention was made with government support under grant number CA094829 awarded by the National Institutes of Health and grant number DAMD17-02-1-0117 awarded by the United States Army Medical Research and Materiel Command. The government has certain rights in the invention.--

Signed and Sealed this
Fourth Day of August, 2020

Andrei Iancu
*Director of the United States Patent and Trademark Office*